(12) United States Patent
Oka

(10) Patent No.: US 6,491,638 B2
(45) Date of Patent: Dec. 10, 2002

(54) CIRCULATION-CONDITION MONITORING APPARATUS

(75) Inventor: Tohru Oka, Ichinomiya (JP)

(73) Assignee: Colin Corporation, Komaki (JP)

( * ) Notice: Subject to any disclaimer, the term of this patent is extended or adjusted under 35 U.S.C. 154(b) by 109 days.

(21) Appl. No.: 09/811,502

(22) Filed: Mar. 20, 2001

(65) Prior Publication Data

US 2001/0051773 A1 Dec. 13, 2001

(30) Foreign Application Priority Data

Jun. 9, 2000 (JP) ........................................ 2000-173700

(51) Int. Cl.$^7$ ................................................ A61B 5/02
(52) U.S. Cl. ...................... 600/494; 600/500; 600/496; 600/493; 600/495
(58) Field of Search ................................ 600/494, 500, 600/503, 485, 490, 495, 496, 493, 504

(56) References Cited

U.S. PATENT DOCUMENTS

| | | | | |
|---|---|---|---|---|
| 5,865,756 A | * | 2/1999 | Peel, III | 600/485 |
| 5,895,359 A | * | 4/1999 | Peel, III | 600/494 |
| 5,931,790 A | * | 8/1999 | Peel, III | 600/494 |
| 6,186,953 B1 | * | 2/2001 | Narimatsu | 128/925 |
| 6,241,680 B1 | * | 6/2001 | Miwa | 600/490 |
| 6,331,162 B1 | * | 12/2001 | Mitchell | 600/485 |
| 6,423,010 B1 | * | 6/2002 | Friedman et al. | 600/494 |

FOREIGN PATENT DOCUMENTS

JP      64-56206      4/1989

* cited by examiner

*Primary Examiner*—Patrick Brinson
(74) *Attorney, Agent, or Firm*—Oliff & Berridge, PLC

(57) ABSTRACT

A blood-circulation monitor including a heartbeat-synchronous-wave sensor, a first judging device for judging whether an arrhythmia has occurred to a living subject, based on a heartbeat-synchronous wave detected by the sensor, a first determining device including a cuff and determining a first blood pressure of the subject based on a first pulse wave produced in the cuff, an information obtaining device for iteratively obtaining a piece of blood-pressure-relating information which changes in relation with blood pressure of the subject, a relationship determining device for determining a relationship between blood pressure and blood-pressure-relating information, a second determining device for iteratively determining, according to the relationship, a second blood pressure of the subject based on each of the pieces of blood-pressure-relating information, a calculating device for calculating a change value of the second blood pressure values, and a second judging device for judging that the condition of blood circulation of the subject is abnormal, when the first judging device judges that the arrhythmia has occurred to the subject and when the change value does not fall within a reference range.

14 Claims, 9 Drawing Sheets

CIRCULATION-CONDITION MONITORING APPARATUS

BACKGROUND OF THE INVENTION

1. Field of the Invention

The present invention relates to an apparatus for monitoring a condition of blood circulation of a living subject.

2. Related Art Statement

There is known a circulation-condition monitoring apparatus which includes a heartbeat-synchronous-wave detecting device which is worn on a patient and detects a heartbeat-synchronous wave from the subject; an arrhythmia judging means for judging whether an arrhythmia has occurred to the patient, based on the heartbeat-synchronous wave detected by the heartbeat-synchronous-wave detecting device; and an alarming device which produces an alarming sound when the arrhythmia judging means judges that an arrhythmia has occurred to the patient. For example, there is known a circulation-condition monitoring apparatus which includes an electrocardiograph (i.e., heartbeat-synchronous-wave detecting device) having a plurality of electrodes adapted to be worn at a plurality of prescribed locations on a living subject to detect an electrocardiogram as a heartbeat-synchronous wave; an arrhythmia diagnosing means for automatically diagnosing an arrhythmia of the subject based on the electrocardiogram detected by the electrocardiograph; and an alarming device which produces an alarming sound when it is judged that an arrhythmia has occurred to the subject.

Since an arrhythmia may indicate that the circulation condition of a patient has worsened, the conventional circulation-condition monitoring apparatus produces an alarming sound when it judges that an arrhythmia has occurred to the patient. However, in some cases, an arrhythmia does not indicate that the circulation condition of a patient has worsened. Therefore, if the monitoring apparatus produces an alarming sound each time it judges that an arrhythmia has occurred to a patient, there will be some cases where an alarming sound is produced when the circulation condition of a patient has not worsened. If those cases are too frequent, a medical staff may keep the alarming device turned off. On the other hand, in other cases, an arrhythmia does indicate that the circulation condition of a patient has worsened. Thus, it is not recommended to keep the alarming device off.

Meanwhile, the circulation condition of a patient can be monitored based on his or her blood pressure. Hence, there had been proposed an automatic blood-pressure monitoring apparatus which continuously monitors whether an arrhythmia has occurred to a patient and, when an arrhythmia has occurred to a patient, automatically measures a blood pressure of the patient. An example of this automatic blood-pressure monitoring apparatus is an automatic blood-pressure measuring apparatus disclosed in Japanese Utility Model Application laid open under Publication No. 64-56206. The disclosed automatic blood-pressure measuring apparatus automatically measures, when it is judged that an arrhythmia has occurred to a patient, a blood pressure of the patient, and judges whether the measured blood pressure falls within a prescribed reference range. Since the prior apparatus monitors the circulation condition of a patient based on both arrhythmia and blood pressure, it can considerably accurately monitor the same.

However, there are some cases where, in a state in which an arrhythmia has occurred to a patient, a blood pressure whose value is normal in a state in which the patient has no arrhythmia indicates, in fact, that the patient needs an urgent treatment. That is, there are some cases where the automatic blood-pressure measuring apparatus disclosed in the above-indicated document does not judge that an abnormality has occurred to a patient but, in fact, the circulation condition of the patient is abnormal and the patient needs an argent treatment. Thus, the accuracy with which the automatic blood-pressure measuring apparatus monitors the circulation condition of the patient is not sufficiently high.

SUMMARY OF THE INVENTION

It is therefore an object of the present invention to provide a blood-circulation monitoring apparatus which can accurately monitor a condition of blood circulation of a living subject.

The Inventor has carried out extensive studies, and has found that if an arrhythmia is caused by an abnormal circulation condition of a living subject, then the blood pressure of the subject exhibits a great change. Therefore, an abnormal circulation condition of the subject can be accurately identified if an arrhythmia is found and simultaneously the blood pressure of the subject exhibits a great change, even if the blood pressure may not exhibit an abnormal value.

In addition, the Inventor has found that an abnormal circulation condition of a living subject can be accurately identified by employing, when an arrhythmia is present, a reference range whose upper and/or lower limit(s) are/is nearer to a normal blood pressure value than the upper and/or lower limits of a reference range which is employed when no arrhythmia is present.

The above object has been achieved by the present invention. According to a first feature of the present invention, there is provided an apparatus for monitoring a condition of blood circulation of a living subject, comprising a heartbeat-synchronous-wave detecting device which detects a heartbeat-synchronous wave from the subject; an arrhythmia judging means for judging whether an arrhythmia has occurred to the subject, based on the heartbeat-synchronous wave detected by the heartbeat-synchronous-wave detecting device; a first blood-pressure determining means including an inflatable cuff which is adapted to be wound around a first body portion of the subject to occlude an artery of the first body portion, the first blood-pressure determining means determining at least one first blood pressure of the subject based on a first pulse wave which is produced in the cuff when a pressure in the cuff is decreased; a blood-pressure-relating-information obtaining means including at least one pulse-wave detecting device which is adapted to be worn on at least one second body portion of the subject to detect at least one second pulse wave from the at least one second body portion without occluding at least one artery of the at least one second body portion, the blood-pressure-relating-information obtaining means iteratively obtaining, based on the at least one second pulse wave detected by the at least one pulse-wave detecting device, a piece of blood-pressure-relating information which changes in relation with blood pressure of the subject; a relationship determining means for determining a relationship between blood pressure and blood-pressure-relating information, based on at least one first blood pressure value determined by the first blood-pressure determining means and at least one piece of blood-pressure-relating information obtained by the blood-pressure-relating-information obtaining means; a second blood-pressure determining means for iteratively determining, according to the relationship determined by the relationship determining means, a second blood pressure of the subject based on each of the pieces of blood-pressure-relating information iteratively obtained by the blood-pressure-relating-information obtaining means; a change-value calculating means for calculating a change value of each of the second blood pressure values iteratively determined by the second blood-pressure determining means; and an abnormality judging means for judging that the condition of blood circulation of the subject is abnormal, when the arrhythmia judging means judges that the arrhythmia has occurred to the subject and when the change value calculated by the change-value calculating means does not fall within a first reference range.

In the present circulation-condition monitoring apparatus, the change-value calculating means calculates a change value of each of the second blood pressure values iteratively determined by the second blood-pressure determining means, and the abnormality judging means judges that the condition of blood circulation of the subject is abnormal, when the arrhythmia judging means judges that the arrhythmia has occurred to the subject and when the change value calculated by the change-value calculating means does not fall within a first reference range. Thus, the present apparatus can accurately monitor the circulation condition of the subject. In addition, the pieces of blood-pressure-relating information can be obtained based on the second pulse wave detected by the pulse-wave detecting device without occluding the artery of the second body portion of the subject, and the second blood pressure values are determined based on the pieces of blood-pressure-relating information. Thus, the present apparatus is free of the disadvantage that each time it is judged that an arrhythmia has occurred to the subject, the first blood pressure determining means is operated to occlude the artery of the first body portion of the subject and thereby cause the subject to feel discomfort.

According to a second feature of the present invention that includes the above-described first feature, the circulation-condition monitoring apparatus further comprises an input device which is operable for inputting a low-blood-pressure-subject signal indicating that the blood pressure of the living subject is low, and the abnormality judging means judges, when the low-blood-pressure-subject signal is input through the input device, that the condition of blood circulation of the subject is abnormal, when the arrhythmia judging means judges that the arrhythmia has occurred to the subject and when at least one of the change value calculated by the change-value calculating means and said each second blood pressure value determined by the second blood-pressure determining means does not fall within a corresponding one of the first reference range and a second reference range. A low-blood-pressure subject exhibits a low blood pressure even when his or her circulation condition may be normal. Therefore, there are some cases where the blood pressure of the subject is so low as to need an urgent treatment even if the change of the blood pressure may not be so great. In the present circulation-condition monitoring apparatus, if the low-blood-pressure-subject signal is input through the input device, then the abnormality judging means judges that the condition of blood circulation of the subject is abnormal, when the arrhythmia judging means judges that the arrhythmia has occurred to the subject and when at least one of the change value calculated by the change-value calculating means and the each second blood pressure value determined by the second blood-pressure determining means does not fall within a corresponding one of the first reference range and a second reference range. Thus, the present apparatus can reliably judge an abnormality of the circulation condition of the subject whose blood pressure is low.

According to a third feature of the present invention, there is provided an apparatus for monitoring a condition of blood circulation of a living subject, comprising a heartbeat-synchronous-wave detecting device which detects a heartbeat-synchronous wave from the subject; an arrhythmia judging means for judging whether an arrhythmia has occurred to the subject, based on the heartbeat-synchronous wave detected by the heartbeat-synchronous-wave detecting device; a blood-pressure measuring means including an inflatable cuff which is adapted to be wound around a body portion of the subject, and iteratively measuring a blood pressure of the subject based on a pulse wave which is produced in the cuff when a pressure in the cuff is changed; a change-value calculating means for iteratively calculating a change value of each of the blood pressure values iteratively measured by the blood-pressure measuring means; and an abnormality judging means for operating, when the arrhythmia judging means judges that the arrhythmia has occurred to the subject, the blood-pressure measuring means to measure a blood pressure of the subject, and the change-value calculating means to calculate a change value of the measured blood pressure value, and judging that the condition of blood circulation of the subject is abnormal, when the change value calculated by the change-value calculating means does not fall within a first reference range.

In the present circulation-condition monitoring apparatus, the abnormality judging means operates, when the arrhythmia judging means judges that the arrhythmia has occurred to the subject, the blood-pressure measuring means to measure a blood pressure of the subject, and the change-value calculating means to calculate a change value of the measured blood pressure value, and judges that the condition of blood circulation of the subject is abnormal, when the change value calculated by the change-value calculating means does not fall within a first reference range. Thus, based on both arrhythmia and blood-pressure change, the present apparatus judges an abnormality of the circulation condition of the subject. Accordingly, the present apparatus can monitor the circulation condition of the subject.

According to a fourth feature of the present invention that includes the above-described third feature, the circulation-condition monitoring apparatus further comprises an input device which is operable for inputting a low-blood-pressure-subject signal indicating that the blood pressure of the living subject is low, and the abnormality judging means operates, when the arrhythmia judging means judges that the arrhythmia has occurred to the subject, the blood-pressure measuring means and the change-value calculating means, and judges that the condition of blood circulation of the subject is abnormal, when at least one of the change value calculated by the change-value calculating means and the blood pressure value measured by the blood-pressure measuring means does not fall within a corresponding one of the first reference range and a second reference range. In the present circulation-condition monitoring apparatus, if the low-blood-pressure-subject signal is input through the input device, then the abnormality judging means operates, when the arrhythmia judging means judges that the arrhythmia has occurred to the subject, the blood-pressure measuring means and the change-value calculating means, and judges that the condition of blood circulation of the subject is abnormal, when at least one of the change value and the blood pressure value does not fall within a corresponding one of the first reference range and the second reference range. Thus, the present apparatus can reliably judge an abnormality of the circulation condition of the subject whose blood pressure is low.

According to a fifth feature of the present invention, there is provided an apparatus for monitoring a condition of blood circulation of a living subject, comprising a heartbeat-synchronous-wave detecting device which detects a heartbeat-synchronous wave from the subject; an arrhythmia judging means for judging whether an arrhythmia has occurred to the subject based on the heartbeat-synchronous wave detected by the heartbeat-synchronous-wave detecting device; a blood-pressure measuring means including an inflatable cuff which is adapted to be wound around a body portion of the subject, and measuring a first blood pressure of the subject based on a pulse wave which is produced in the cuff when a pressure in the cuff is changed; a first abnormality judging means for judging that the condition of blood circulation of the subject is abnormal, when the first blood pressure value measured by the blood-pressure measuring means is not greater than a first reference value; and a second abnormality judging means for operating, when the arrhythmia judging means judges that the arrhythmia has occurred to the subject, the blood-pressure measuring means to measure a second blood pressure of the subject, and judging that the condition of blood circulation of the subject is abnormal, when the second blood pressure value measured by the blood-pressure measuring means is not greater than a second reference value greater than the first reference value.

In present circulation-condition monitoring apparatus, the first abnormality judging means judges that the condition of blood circulation of the subject is abnormal, when the first blood pressure value measured by the blood-pressure measuring means is not greater than a first reference value. In addition, even if the first abnormality judging means does not judge that the condition of blood circulation of the subject is abnormal, the second abnormality judging means operates, when the arrhythmia judging means judges that the arrhythmia has occurred to the subject, the blood-pressure measuring means to measure a second blood pressure of the subject, and judges that the condition of blood circulation of the subject is abnormal, when the second blood pressure value measured by the blood-pressure measuring means is not greater than a second reference value greater than the first reference value. Thus, the present apparatus can accurately judge an abnormality of the circulation condition of the subject.

According to a sixth feature of the present invention, there is provided an apparatus for monitoring a condition of blood circulation of a living subject, comprising a heartbeat-synchronous-wave detecting device which detects a heartbeat-synchronous wave from the subject; an arrhythmia judging means for judging whether an arrhythmia has occurred to the subject based on the heartbeat-synchronous wave detected by the heartbeat-synchronous-wave detecting device; a first blood-pressure determining means including an inflatable cuff which is adapted to be wound around a first body portion of the subject to occlude an artery of the first body portion, the first blood-pressure determining means determining at least one first blood pressure of the subject based on a first pulse wave which is produced in the cuff when a pressure in the cuff is decreased; a blood-pressure-relating-information obtaining means including at least one pulse-wave detecting device which is adapted to be worn on at least one second body portion of the subject to detect at least one second pulse wave from the at least one second body portion without occluding at least one artery of the at least one second body portion, the blood-pressure-relating-information obtaining means iteratively obtaining, based on the at least one second pulse wave detected by the at least one pulse-wave detecting device, a piece of blood-pressure-relating information which changes in relation with blood pressure of the subject; a relationship determining means for determining a relationship between blood pressure and blood-pressure-relating information, based on at least one first blood pressure value determined by the first blood-pressure determining means and at least one piece of blood-pressure-relating information obtained by the blood-pressure-relating-information obtaining means; a second blood-pressure determining means for iteratively determining, according to the relationship determined by the relationship determining means, a second blood pressure of the subject based on each of a plurality of pieces of blood-pressure-relating information iteratively obtained by the blood-pressure-relating-information obtaining means; a first abnormality judging means for judging that the condition of blood circulation of the subject is abnormal, when a first blood pressure value determined by the first blood-pressure determining means is not greater than a first reference value; and a second abnormality judging means for judging that the condition of blood circulation of the subject is abnormal, when the arrhythmia judging means judges that the arrhythmia has occurred to the subject and when a second blood pressure value determined by the second blood-pressure determining means is not greater than a second reference value greater than the first reference value.

In present circulation-condition monitoring apparatus, the first abnormality judging means judges that the condition of blood circulation of the subject is abnormal, when the first blood pressure value measured by the blood-pressure measuring means is not greater than a first reference value. In addition, even if the first abnormality judging means does not judge that the condition of blood circulation of the subject is abnormal, the second abnormality judging means judges that the condition of blood circulation of the subject is abnormal, when the arrhythmia judging means judges that the arrhythmia has occurred to the subject and when the second blood pressure value measured by the second blood-pressure determining means is not greater than a second reference value greater than the first reference value. Thus, the present apparatus can accurately monitor the circulation condition of the subject. In addition, the pieces of blood-pressure-relating information can be obtained based on the second pulse wave detected by the pulse-wave detecting device without occluding the artery of the second body portion of the subject, and the second blood pressure values are determined based on the pieces of blood-pressure-relating information. Thus, the present apparatus is free of the disadvantage that each time it is judged that an arrhythmia has occurred to the subject, the first blood pressure determining means is operated to occlude the artery of the first body portion of the subject and thereby cause the subject to feel discomfort.

According to a seventh feature of the present invention that includes any of the above-described first to sixth features, the heartbeat-synchronous-wave detecting device comprises an electrocardiograph which includes a plurality of electrodes that are adapted to be worn at a plurality of prescribed locations on the living subject and which detects, as the heartbeat-synchronous wave, an electrocardiogram through the electrodes. In this apparatus, the electrocardiograph detects electrocardiogram of the subject, and the arrhythmia judging means judges, based on the detected electrocardiogram, whether an arrhythmia has occurred to the subject. Thus, the arrhythmia judging means can identify various sorts of arrhythmias.

According to an eighth feature of the present invention that includes any of the above-described first to sixth features, the heartbeat-synchronous-wave detecting device comprises the inflatable cuff and detects, as the heartbeat-synchronous wave, the pulse wave which is produced in the cuff in a state in which the pressure in the cuff is equal to a pre-set value lower than a diastolic blood pressure value of the living subject. In this apparatus, the cuff as part of the first blood-pressure determining means is used to detect the heartbeat-synchronous wave. Thus, the present circulation-condition monitoring apparatus can enjoy a simple construction, and can be produced at reduced cost.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
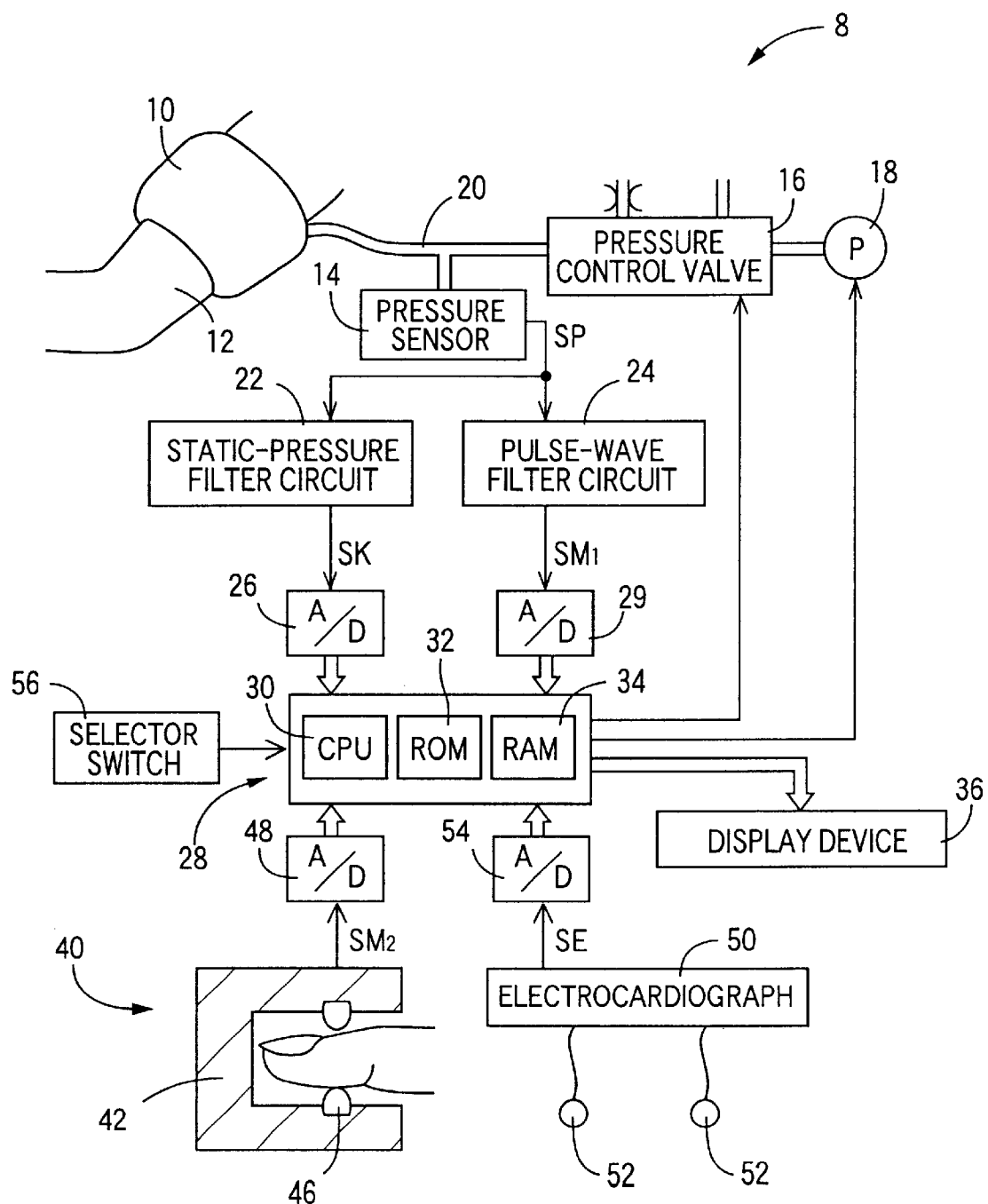
FIG. 1 is a diagrammatic view for explaining a construction of a circulation-condition monitoring apparatus embodying the present invention.

Hereinafter, there will be described a preferred embodiment of the present invention, by reference to the drawings. FIG. 1 is a diagrammatic view for explaining the construction of a circulation-condition monitoring apparatus 8 to which the present invention is applied.

In FIG. 1, the circulation-condition monitoring apparatus 8 includes an inflatable cuff 12 which includes a belt-like cloth bag and a rubber bag accommodated in the cloth bag and which is adapted to be wound around an upper arm 12 of a patient as a living subject. The cuff 10 is connected via a piping 20 to a pressure sensor 14, a pressure control valve 16, and an air pump 18. The pressure control valve 16 is constructed such that it is selectively placed in one of the following three positions: the first position is a pressure-supply position in which the valve 16 permits pressurized air to be supplied from the air pump 18 to the cuff 10; the second position is a slow-deflation position in which the valve 16 permits the pressurized air to be slowly deflated from the cuff 10; and the third position is a quick-deflation position in which the valve 16 permits the pressurized air to be quickly deflated from the cuff 10.

The pressure sensor 14 detects a pressure in the cuff 10, and supplies a pressure signal SP representing the detected pressure, to each of a static-pressure filter circuit 22 and a pulse-wave filter circuit 24. The static-pressure filter circuit 22 includes a low-pass filter which extracts, from the pressure signal SP, a cuff pressure signal SK representing a cuff pressure $P_C$ as a constant component of the pressure signal SP, and supplies the cuff pressure signal SK to an electronic control device 28 via an analog-to-digital (A/D) converter 26.

The pulse-wave filter circuit 24 includes a band-pass filter which extracts, from the pressure signal SP, a cuff pulse wave signal $SM_1$ representing a cuff pulse wave as a frequency component of the pressure signal SP, and supplies the cuff pulse wave signal $SM_1$ to the control device 28 via an A/D converter 29. The cuff pulse wave represented by the cuff pulse wave signal $SM_1$ is a brachial pulse wave which is produced from a brachial artery, not shown, of the patient in synchronism with heartbeat of the patient and is transmitted to the cuff 10.

The control device 28 is essentially provided by a so-called microcomputer including a central processing unit (CPU) 30, a read only memory (ROM) 32, a random access memory (RAM) 34, an input-and-output (I/O) port, not shown, etc. The control device 28 or the CPU 30 processes signals according to control programs pre-stored in the ROM 32, while utilizing a temporary-storage function of the RAM 34, and monitors a circulation condition of the patient. In addition, the CPU 30 controls what is displayed by a display device 36.

The present apparatus 8 additionally includes a photoelectric-pulse-wave sensor 40 functioning as a volumetric-pulse-wave detecting device which detects a volumetric pulse wave (i.e., plethysmogram) from peripheral blood vessels of the patient. The sensor 40 is worn on, e.g., an end portion of a finger of the other arm of the patient than the arm 12 around which the cuff 12 is wound. The pulse-wave sensor 40 includes a housing 42 which can accommodate a body portion of the patient, such as an end portion of a finger; a light emitting element 44 as a light source which emits, toward a skin of the patient, a red or infrared light in such a wavelength band that can be reflected by hemoglobin, preferably a light having a wavelength of about 800 nm that is not influenced by blood oxygen saturation; and a light receiving element 46 which is provided on a side of the housing 42 that is opposite to the light emitter 44 and which detects the light transmitted through the body portion of the patient. The sensor 40 outputs a photoelectric-pulse-wave signal $SM_2$ representing an instantaneous volume of blood present in capillaries of the body portion, and supplies the signal $SM_2$ to the control device 28 via an A/D converter 48.

An electrocardiograph device 50 includes a plurality of electrodes 52 which are adapted to be adhered to a plurality of prescribed locations on the patient, and continuously detects, through the electrodes 52, an electrocardiographic waveform, i.e., a so-called electrocardiogram representing an action potential of the cardiac muscle of the patient. The device 50 supplies, to the control device 28 via an A/D converter 54, an electrocardiogram signal SE representing the detected electrocardiogram. Since the electrocardiogram is a heartbeat-synchronous wave which is produced in synchronism with heartbeat of the patient, the electrocardiograph device 50 functions as a heartbeat-synchronous-wave detecting device.

A selector switch 56 functions as an input device in the present embodiment. The selector switch 56 is selectively switchable to a first position in which the switch 56 outputs a low-blood-pressure-patient signal indicating that the current patient is a low-blood-pressure patient, and to a second position in which the switch 56 outputs a different signal indicating that the current patient is not a low-blood-pressure patient. When a doctor etc. diagnoses that the patient is a low-blood-pressure patient, he or she operates the selector switch 56 to its first position before the present apparatus 8 is started to monitor the circulation condition of the patient. However, even if a doctor may not diagnose that the patient is a low-blood-pressure patient, he or she may operate the selector switch 56 to its first position. A low-blood-pressure patient is defined as a patient whose systolic blood pressure is low, e.g., not higher than 100 mmHg, when he or she is in good shape.

Figure 2:
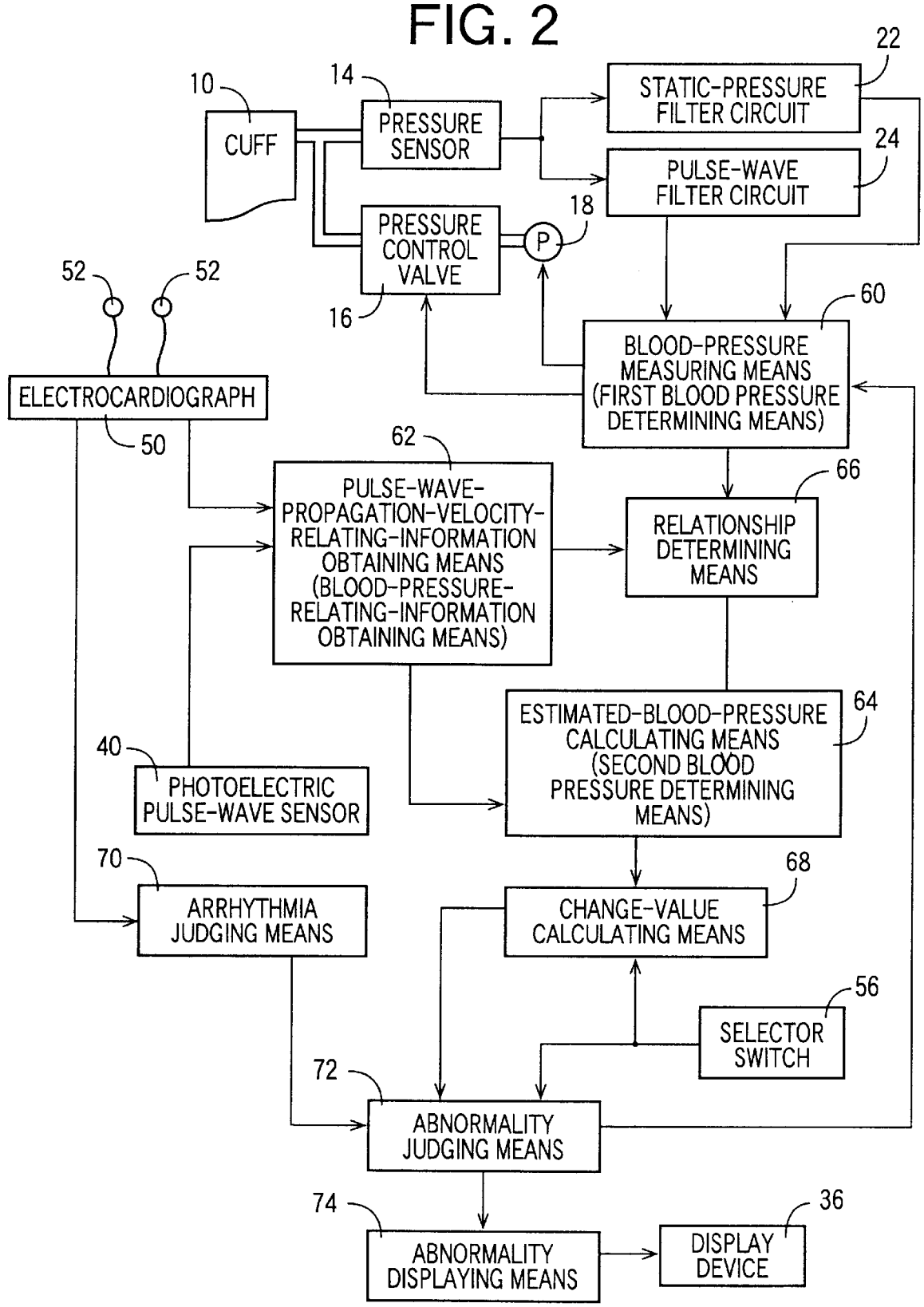
FIG. 2 is a block diagram for explaining essential functions of an electronic control device of the circulation-condition monitoring apparatus of FIG. 1.

FIG. 2 is a block diagram for explaining important functions of the control device 28. In the figure, a blood-pressure measuring means 60 functioning as a first blood-pressure determining means first operates the air pump 18 and switches the pressure control valve 16 to its pressure-supply position, so that the pressure in the cuff 12 is quickly increased. In addition, when the cuff pressure signal SK extracted by the static-pressure filter circuit 22 indicates that the pressure of the cuff 12 has reached a prescribed target pressure value $P_{CM}$ (e.g., about 180 mmHg) higher than a systolic blood pressure of the patient, the measuring means 60 switches the control valve 16 to its slow-deflation position, so that the pressure of the cuff 12 is slowly decreased at a prescribed low rate of about 3 mmHg/sec. And, the blood-pressure measuring means 60 determines, according to a well-known oscillometric method, a systolic blood pressure $BP_{SYS}$, a mean blood pressure $BP_{MEAN}$, and a diastolic blood pressure $BP_{DIA}$ of the patient, based on the change of respective amplitudes of heartbeat-synchronous pulses of the cuff pulse wave represented by the cuff pulse wave signal $SM_1$ which is continuously produced during the slow decrease or deflation of the cuff 12.

Figure 3:
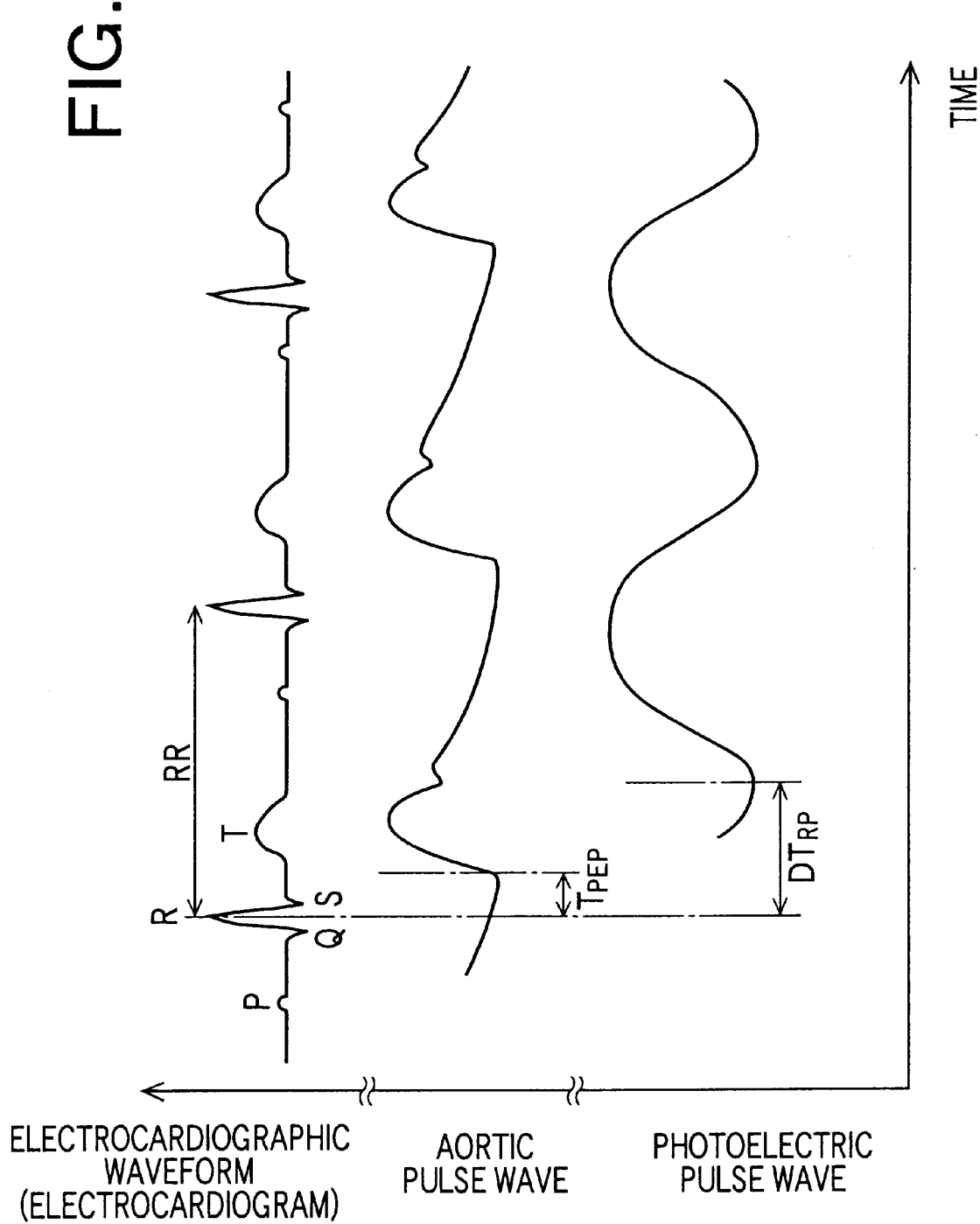
FIG. 3 is a graph for explaining a pulse-wave propagation time $DT_{RP}$ which is obtained by the control device of the circulation-condition monitoring apparatus of FIG. 1.

A pulse-wave-propagation-velocity-relating information obtaining means 62 includes a time-difference determining means which iteratively determines, as illustrated in FIG. 3, a time difference (i.e., pulse-wave propagation time) $DT_{RP}$ between a prescribed periodic point (e.g., R-wave) on each of successive heartbeat-synchronous pulses of the electrocardiographic waveform (i.e., electrocardiogram or ECG) continuously detected by the electrocardiograph 50, and a prescribed periodic point (e.g., rising point or minimum point) on each of successive heartbeat-synchronous pulses of the photoelectric pulse wave continuously detected by the photoelectric-pulse-wave sensor 40. The information obtaining means 62 iteratively calculates, based on each of the time difference values $DT_{RP}$ determined by the time-difference determining means, a pulse-wave propagation velocity PWV (m/sec) at which a pulse wave propagates through an artery of the patient, according to the following expression (1) pre-stored in the ROM 32:

$$PWV=L/(DT_{RP}-T_{PEP}) \quad (1)$$

where L (m) is the distance from the left ventricle via the aorta to the position where the sensor 40 is worn; and $T_{PEP}$ (sec) is a pre-ejection time from an R-wave of the electrocardiogram to a minimum point of an aortic pulse wave detected from an initial portion of the aorta.

In the above expression (1), L and $T_{PEP}$ are constants which are experimentally obtained in advance. It is known that each of pulse-wave propagation time $DT_{RP}$ and pulse-wave propagation velocity PWV of a living subject changes in relation with blood pressure BP of the subject. Thus, the pulse-wave-propagation-velocity-relating information obtained by the information obtaining means 62 is a sort of blood-pressure-relating information, and the information obtaining means 62 functions as a blood-pressure-relating-information obtaining means.

An estimated-blood-pressure calculating means 64 functioning as a second blood-pressure determining means iteratively calculates, based on each of a plurality of pieces of pulse-wave-propagation-velocity-relating information (e.g., the pulse-wave propagation time values $DT_{RP}$, or the pulse-wave propagation velocity values PWV), iteratively obtained by the information obtaining means 62, an estimated blood pressure value EBP of the patient, according to a predetermined relationship between estimated blood pressure EBP and pulse-wave-propagation-velocity-relating information, e.g., relationship represented by the following expression (2) or (3):

$$EBP=\alpha(1/DT_{RP})+\beta \quad (2)$$

$$EBP=\alpha'PWV+\beta' \quad (3)$$

In the above expressions (2) and (3), $\alpha$, $\beta$, $\alpha'$, $\beta'$ are all constants. Since pulse-wave propagation time $DT_{RP}$ decreases (and, inverse of time, $1/DT_{RP}$, increases) as blood pressure BP increases, constant $\alpha$ is positive; and since pulse-wave propagation velocity PWV increases as blood pressure BP increases, constant $\alpha'$ is positive. The estimated-blood-pressure calculating means 64 stores the thus calculated estimated blood pressure values EBP in a prescribed memory area, not shown, of the RAM 34.

A relationship determining means 66 determines each or one of the two constants of each or one of the two expressions (2), (3), based on at least one systolic blood pressure value $BP_{SYS}$ measured by the blood-pressure measuring means 60 and at least one piece of pulse-wave-propagation-relating information obtained by the information obtaining means 62 when the at least one systolic blood pressure value $BP_{SYS}$ was measured by the measuring means 66 (i.e., during the blood-pressure measuring operation in which the one systolic blood pressure value $BP_{SYS}$ was measured, or immediately before or after the blood-pressure measuring operation). For example, the relationship determining means 66 determines (or updates), in advance, either one of the two constants $\alpha$, $\beta$ of the expression (2), based on one systolic blood pressure value $BP_{SYS}$ measured by the blood-pressure measuring means 60 and one pulse-wave propagation time $DT_{RP}$ obtained by the information obtaining means 62 during the blood-pressure measuring operation in which the one systolic blood pressure value $BP_{SYS}$ was measured. Alternatively, the relationship determining means 66 may determine (or update), in advance, each of the two constants $\alpha$, $\beta$ of the expression (2), based on a first combination of one systolic blood pressure value $BP_{SYS}$ measured by the measuring means 60 in the current blood-pressure measuring operation and one pulse-wave propagation time $DT_{RP}$ obtained during the current blood-pressure measuring operation, and a second combination of one systolic blood pressure value $BP_{SYS}$ measured in the preceding blood-pressure measuring operation and one pulse-wave propagation time $DT_{RP}$ obtained during the preceding blood-pressure measuring operation. In place of systolic blood pressure value $BP_{SYS}$, the relationship determining means 66 may utilize mean blood pressure value $BP_{MEAN}$ or diastolic blood pressure value $BP_{DIA}$, measured by the measuring means 60, for determining the relationship. That is, when the estimated-blood-pressure calculating means 64 calculates estimated mean blood pressure values of the patient, the relationship determining means 66 utilizes the mean blood pressure value $BP_{MEAN}$; and when the calculating means 64 calculates estimated diastolic blood pressure values of the patient, the relationship determining means 66 utilizes the diastolic blood pressure value $BP_{DIA}$.

A change-value calculating means 68 calculates a change value ΔEBP of the estimated blood pressure values EBP iteratively calculated by the estimated-blood-pressure calculating means 64. Here, change value ΔEBP is defined as a change rate (%) or a change amount (mmHg) of each of the estimated blood pressure values EBP iteratively calculated by the means 64. For example, change value ΔEBP may be defined as a change rate or a change amount of each estimated blood pressure value EBP with respect to a moving average $EBP_{AV}$ of estimated blood pressure values EBP obtained during a predetermined number (e.g., from 20 to 30) of heartbeats or a prescribed time duration (e.g., from 30 seconds to several minutes). Alternatively, change value ΔEBP may be defined as a change rate or a change amount of each estimated blood pressure value EBP with respect to an estimated blood pressure value EBP obtained immediately after the last blood-pressure measuring operation of the blood-pressure measuring means 60, or an estimated blood pressure value EBP obtained a prescribed time duration (e.g., 10 minutes) or a prescribed number of heartbeats before.

An arrhythmia judging means 70 judges, based on the electrocardiogram signal SE supplied from the electrocardiograph 50, whether an arrhythmia has occurred, according to a well-known arrhythmia judging algorithm. For example, the arrhythmia judging means 70 compares the electrocardiographic waveform represented by the electrocardiogram signal SE, with a normal electrocardiographic waveform which is pre-stored in the ROM 32, and judges that an arrhythmia has occurred if a level of a flat S-T interval (i.e., S-T level) of the detected electrocardiographic waveform has increased, or decreased, from a normal S-T level by more than a prescribed threshold value, or when a ventricular extrasystole has occurred. Various sorts of ventricular extrasystoles are known, such as multiple ventricular extrasystole wherein more than five or six ventricular extrasystoles occur per minute; R-on-T ventricular extrasystole wherein extrasystolic R-wave overlaps normal T-wave preceding the R-wave; or short-run ventricular extrasystole wherein more than three or four ventricular extrasystoles successively occur. The arrhythmia judging means 70 identifies each sort of ventricular extrasystole by comparing the detected electrocardiographic waveform with the pre-stored normal electrocardiographic waveform. In addition, the arrhythmia judging means 70 determines a pulse period $T_P$ based on the detected electrocardiographic waveform, and identifies an arrhythmia, such as tachycardia wherein the determined pulse period $T_P$ is abnormally short, or bradycardia wherein the pulse period $T_P$ is abnormally long.

An abnormality judging means 72 judges that the circulation condition of the patient is abnormal, when the arrhythmia judging means 70 judges that an arrhythmia has occurred and simultaneously when a change value ΔEBP calculated by the change-value calculating means 68 when the arrhythmia judging means 70 judged that arrhythmia occurred is greater than a prescribed reference value TH(Δ) as upper and lower limits of a prescribed reference range. When the abnormality judging means 72 judges that the circulation condition of the patient is abnormal, the judging means 72 starts the blood-pressure measuring means 60 so as to measure a reliable blood pressure value or values BP of the patient. The above-indicated change value Δ EBP, calculated when the arrhythmia judging means 70 judged that arrhythmia has occurred, may be the last one of the change values ΔEBP which had already been calculated when the judging means 70 judged that arrhythmia has occurred, or a change values ΔEBP which is calculated immediately after the judging means 70 judged that arrhythmia has occurred. The above-indicated reference value TH(Δ) may be a value which is experimentally obtained in advance. More specifically described, in the case where change values ΔEBP are change rates, the reference value TH(Δ) may be from 20 to 30%; and in the case where change values ΔEBP are change amounts, the reference value TH(Δ) may be from 20 to 30 mmHg. When the estimated blood pressure values EBP are decreasing, the change values Δ EBP take a negative sign. Hence, the abnormality judging means 72 makes a judgment by comparing an absolute value of each change value ΔEBP with the positive reference value TH(Δ) as both the upper and lower limits of the reference range. Thus, the abnormality judging means 72 may judge, when an arrhythmia occurs, an abnormality of circulation condition of the patient, not only when the blood pressure of the patient is increasing but also when the blood pressure is decreasing.

In the case where the low-blood-pressure-patient signal has been input through the selector switch 56, the abnormality judging means 72 judges that the circulation condition of the patient is abnormal, when the arrhythmia judging means 70 judges that arrhythmia has occurred and simultaneously when the change value ΔEBP calculated by the change-value calculating means 68 when it is judged that arrhythmia occurred is greater than the reference value TH(Δ) and/or when the estimated blood pressure value EBP calculated by the estimated-blood-pressure calculating means 64 at the same time as indicted above is lower than a reference value TH(BP). In the case where estimated blood pressure values EBP are systolic blood pressure values, the reference value TH(BP) may be from 80 to 90 mmHg. Low-blood-pressure patients have low blood pressure when they are in good shape. Therefore, even in the case where the change value ΔEBP is not greater than the reference value TH(Δ), the blood pressure of those patients may be so low as to need an urgent treatment. Thus, the abnormality judging means 72 judges that the circulation condition of the patient is abnormal, when the blood pressure of the patient is low.

An abnormality displaying means 74 operates, when the abnormality judging means 72 judges that the circulation condition of the patient is abnormal, the display device 36 to display the indication that the circulation condition of the patient is abnormal.

Figure 4:
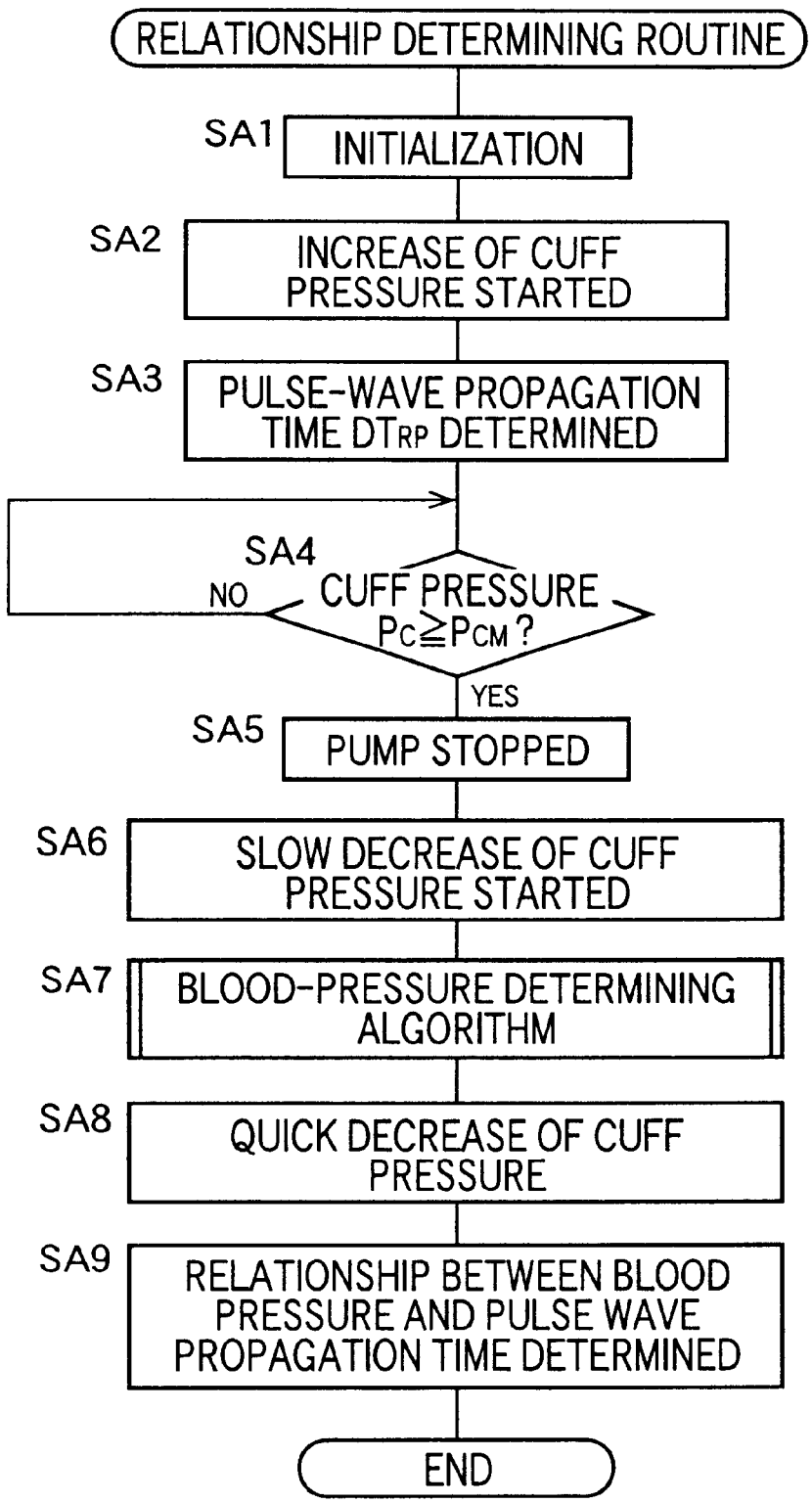
FIG. 4 is a flow chart representing a controlling operation of the control device of the circulation-condition monitoring apparatus of FIG. 1, more specifically, a relationship determining routine according to which the control device determines a relationship which is to be used to calculate estimated blood pressure values EBP.

FIG. 4 shows a flow chart representing a control program according to which the control device 28 controls the circulation-condition monitoring apparatus 8, more specifically, a relationship determining routine according to which the control device 28 determines a relationship or expression which is to be used for calculating estimated blood pressure values EBP of the patient. First, at Step SA1, the control device 28 initializes the apparatus 8, for example, resets a timer, t, and various registers. Then, at Step SA2, the control device 28 switches the pressure control valve 16 to its pressure-supply position, and operates the air pump 18, so as to start a quick increase of the pressure of the cuff 10, thereby starting a blood-pressure measuring operation.

Subsequently, at Step SA3 corresponding to the pulse-wave-propagation-velocity-relating-information obtaining means 64, the control device 28 determines, as illustrated in FIG. 3, a pulse-wave propagation time $DT_{RP}$, i.e., a time difference between a time of occurrence of an R-wave of each of successive heartbeat-synchronous pulses of the electrocardiographic waveform and a time of occurrence of a rising point of a corresponding one of successive heartbeat-synchronous pulses of the photoelectric pulse wave continuously detected by the photoelectric pulse-wave sensor 40.

Then, at Step SA4, the control device 28 judges whether the cuff pressure $P_C$ has reached a prescribed target pressure value $P_{CM}$ of about 180 mmHg. If a negative judgment is made at Step SA4, Step SA4 is repeated, while the cuff pressure $P_C$ is continuously increased. On the other hand, if a positive judgment is made at Step SA4, the control of the control device 28 proceeds with Step SA5 to stop the air pump 18, and then with Step SA6 to switch the pressure control valve 16 to its slow-deflation position, so as to start a slow decrease of the pressure of cuff 10 at a prescribed low rate of about 3 mmHg/sec.

At Step SA7, the control device 28 sequentially determines, based on the change of respective amplitudes of heartbeat-synchronous pulses of the cuff pulse wave represented by the cuff pulse wave signal $SM_1$ obtained during the slow deflation of the cuff 10, a systolic blood pressure value $BP_{SYS}$, a mean blood pressure value $BP_{MEAN}$, and a diastolic blood pressure value $BP_{DIA}$ of the patient, according to the well-known oscillometric blood-pressure determining algorithm. After the determination of the diastolic blood pressure value $BP_{DIA}$, the control goes to Step SA8 to switch the pressure control valve 16 to its quick-deflation position, thereby quickly decreasing the pressure of the cuff 10. Thus, Steps SA2 and SA4 to SA8 correspond to the blood-pressure measuring means 60.

Step SA8 is followed by Step SA9 corresponding to the relationship determining means 66. At Step SA9, the control device 28 determines or updates the two constants α, β of the expression (2), based on a first combination of one systolic blood pressure value $BP_{SYS}$ measured at Step SA7 in the current blood-pressure measuring operation, i.e., in the current control cycle according to the routine of FIG. 4 and one pulse-wave propagation time $DT_{RP}$ obtained at Step SA3 during the current blood-pressure measuring operation, and a second combination of one systolic blood pressure value $BP_{SYS}$ measured in the preceding blood-pressure measuring operation, i.e., in the preceding control cycle according to the routine of FIG. 4 and one pulse-wave propagation time $DT_{RP}$ obtained during the preceding blood-pressure measuring operation. However, when the control device 28 operates in an initial control cycle according to the routine of FIG. 4 after the present circulation-condition monitoring apparatus 8 is started, the control device 28 uses, as one of the two constants α, β, a general purpose value which is statistically obtained in advance and is pre-stored in the ROM 32.

Figure 5:
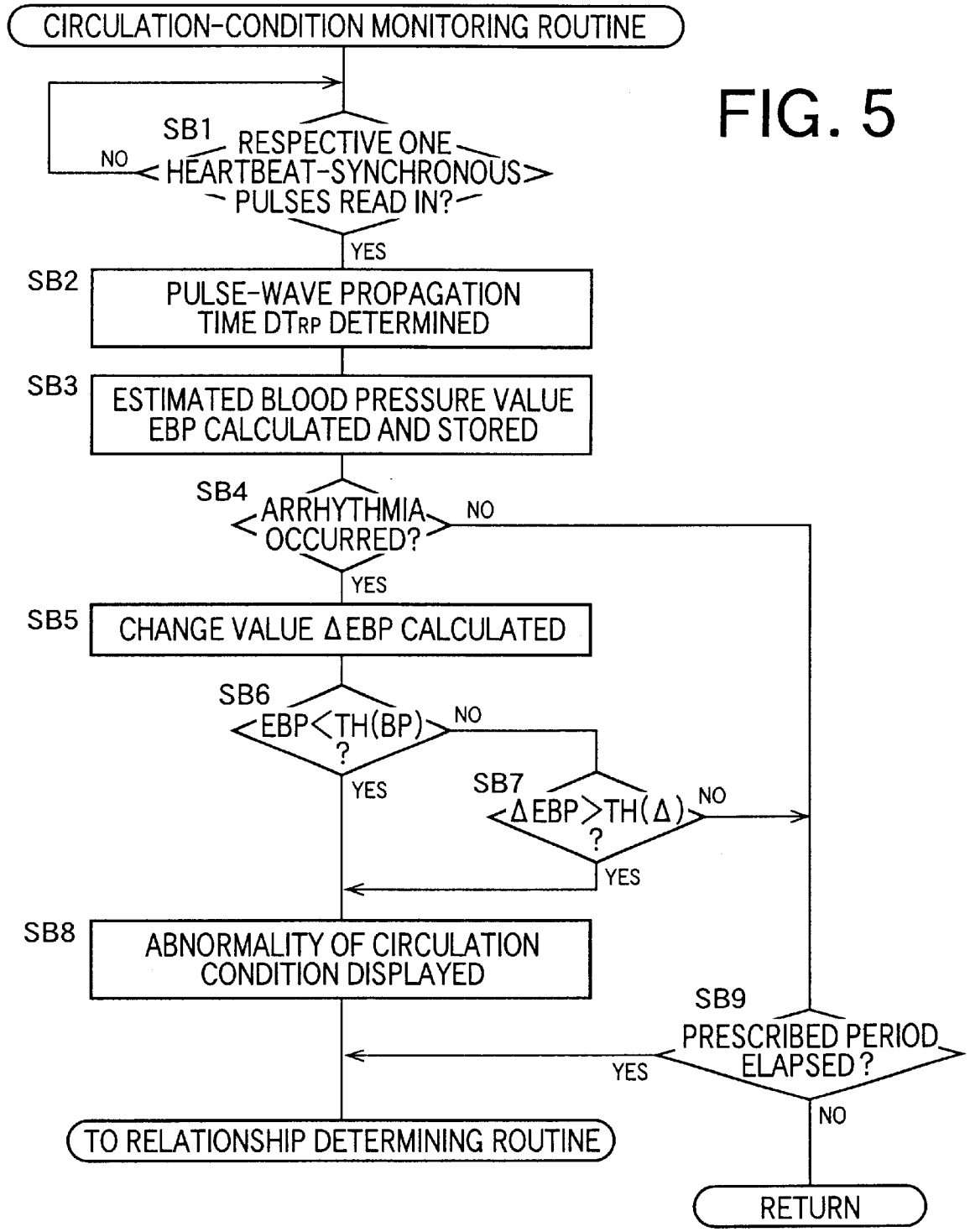
FIG. 5 is a flow chart representing another controlling operation of the control device of the circulation-condition monitoring apparatus of FIG. 1, more specifically, a circulation-condition monitoring routine which is carried out by the control device after the relationship determining routine of FIG. 4.

FIG. 5 shows a flow chart representing another control program according to which the control device 28 controls, after the relationship determining routine of FIG. 4, the circulation-condition monitoring apparatus 8, more specifically, a circulation-condition monitoring routine according to which the control device 28 monitors the circulation condition of the patient. The circulation-condition monitoring routine of FIG. 5 is for low-blood-pressure patients, that is, a routine which is used when the low-blood-pressure-patient signal is input through the selector switch 56.

First, at Step SB1, the control device 28 judges whether it has read in respective one heartbeat-synchronous pulses of the electrocardiogram signal SE continuously supplied from the electrocardiograph 50 and the photoelectric-pulse-wave signal $SM_2$ continuously supplied from the photoelectric-pulse-wave sensor 40, for example, judges whether it has read in a maximum point of one heartbeat-synchronous pulse of the pulse-wave signal $SM_2$ continuously supplied from the pulse-wave sensor 40. If a negative judgment is made at Step SB1, Step SB1 is repeated, while the signals SE, $SM_2$ are continuously read in.

On the other hand, if a positive judgment is made at Step SB1, the control of the control device 28 goes to Step SB2 corresponding to the pulse-wave-propagation-velocity-relating-information obtaining means 62. At Step SB2, the control device 28 determines, based on the respective heartbeat-synchronous pulses of the electrocardiogram signal SE and the photoelectric-pulse-wave signal $SM_2$ read in at Step SB1, a pulse-wave-propagation time $DT_{RP}$, i.e., a time difference between a time of occurrence of an R-wave of the one heartbeat-synchronous pulse of the signal SE and a time of occurrence of a rising point of the one heartbeat-synchronous pulse of the signal $SM_2$.

Subsequently, at Step SB3 corresponding to the estimated-blood-pressure calculating means 64, the control device 28 calculates an estimated blood pressure EBP of the patient, by replacing, with the pulse-wave-propagation time $DT_{RP}$ determined at Step SB2, the variable $DT_{RP}$ in the expression (2) whose constants α, β, have been determined at Step SA9 of FIG. 4, and stores the thus calculated estimated blood pressure value EBP in a prescribed memory area of the RAM 34.

At Step SB4 corresponding to the arrhythmia judging means 70, the control device 28 judges whether an arrhythmia has occurred to the patient, by comparing the waveform of a prescribed length of the electrocardiogram signal SE including the one heartbeat-synchronous pulse read in at Step SB1, with a normal electrocardiographic waveform which is pre-stored in the ROM 32.

If a positive judgment is made at Step SB4, the control goes to Step SB5 corresponding to the change-value calculating means 68. At Step SB5, the control device 28 calculates, as a change value ΔEBP of the current estimated blood pressure value EBP calculated at Step SB3, a rate (%) of change of the current estimated value EBP from a past estimated blood pressure value EBP calculated at Step SB3 immediately after the current relationship (i.e., expression (2)) was determined or updated at Step SA9. For example, the control device 28 determines the rate of change of the current estimated value EBP by dividing a value obtained by subtracting the past estimated value EBP from the current estimated value EBP, by the past estimated value EBP.

Then, the control device 28 carries out Steps SB6 and SB7 corresponding to the abnormality judging means 74. First, at Step SB6, the control device 28 judges whether the current estimated blood pressure value EBP calculated at Step SB3 is smaller than 80 mmHg as the prescribed reference value TH(BP). If a negative judgment is made at Step SB6, the control goes to Step SB7 to judge whether the change value ΔEBP calculated at Step SB5 is greater than 20% as the prescribed reference value TH(Δ). If a positive judgment is made at Step SB6 or SB7, the control goes to Step SB8 corresponding to the abnormality displaying means 74. At Step SB8, the control device 28 operates the display device 36 to display an indication that the circulation condition of the current patient is abnormal, and then carries out the relationship determining routine of FIG. 4 to perform a new blood-pressure measuring operation using the cuff 10 and thereby obtain a more reliable blood pressure value or values of the patient.

On the other hand, if a negative judgment is made at Step SB4 or Step SB7, the control goes to Step SB9 to judge whether a time which has passed after the current relationship was determined at Step SA9 of the relationship determining routine of FIG. 4 has reached a prescribed calibration period of from 15 to 20 minutes. If a negative judgment is made at Step SB9, Steps SB1 and the following steps of the circulation-condition monitoring routine are repeated. On the other hand, if a positive judgment is made at Step SB9, the relationship determining routine of FIG. 4 is carried out again to update the relationship represented by the expression (2).

In the illustrated embodiment, the change-value calculating means 68 (Step SB5) calculates the change value ΔEBP of each of the estimated blood pressure values EBP calculated by the estimated-blood-pressure calculating means 64 (Step SB3); the abnormality judging means 72 (Steps SB6, SB7) judges that the circulation condition of the patient is abnormal, when the arrhythmia judging means 70 (Step SB4) judges that arrhythmia has occurred and simultaneously when the change value ΔEBP calculated by the change-value calculating means 68 (Step SB5) is greater than the prescribed reference value TH(Δ). Thus, the present apparatus 8 can accurately monitor the circulation condition of the patient. In addition, the pulse-wave propagation time $DT_{RP}$ is determined based on the photoelectric pulse wave and the electrocardiogram which are detected by the photoelectric pulse-wave sensor 40 and the electrocardiograph 50 without occluding the arteries, and the estimated blood pressure value EBP is calculated based on the thus determined pulse-wave propagation time $DT_{RP}$. Thus, the present apparatus 8 does not always occlude the arteries of the subject when the arrhythmia judging means 70 (Step SB4) judges that arrhythmia has occurred. Accordingly, the discomfort the patient feels is reduced as such.

In addition, in the illustrated embodiment, in the case where the low-blood-pressure-patient signal is input through the selector switch 56, the abnormality judging means 72 (Steps SB6, SB7) judges, when the arrhythmia judging means 70 (Step SB4) judges that arrhythmia has occurred, that the circulation condition of the patient is abnormal, when the change value ΔEBP calculated by the change-value calculating means 68 (Step SB5) is greater than the prescribed first reference value TH(Δ) and/or when the estimated blood pressure value EBP calculated by the estimated blood-pressure calculating means 64 (Step SB3) is lower than the prescribed second reference value TH(BP). Thus, the present apparatus 8 can reliably monitor the circulation condition of the patient whose blood pressure is low.

In addition, in the illustrated embodiment, the electrocardiograph 50 is used as the heartbeat-synchronous-wave detecting device. The electrocardiogram signal SE produced by the electrocardiograph 50 represents the electrocardiogram based on which the arrhythmia judging means 70 (Step SB4) judges whether arrhythmia has occurred to the patient. Thus, the present apparatus 8 can identify various sorts of arrhythmia.

Next, there will be described a second embodiment of the present invention that also relates to a circulation-condition monitoring apparatus. In the following description of the second embodiment, the same reference numerals as used in the description of the first embodiment are used to designate the corresponding elements and parts of the second embodiment, and detailed description thereof is omitted.

Figure 6:
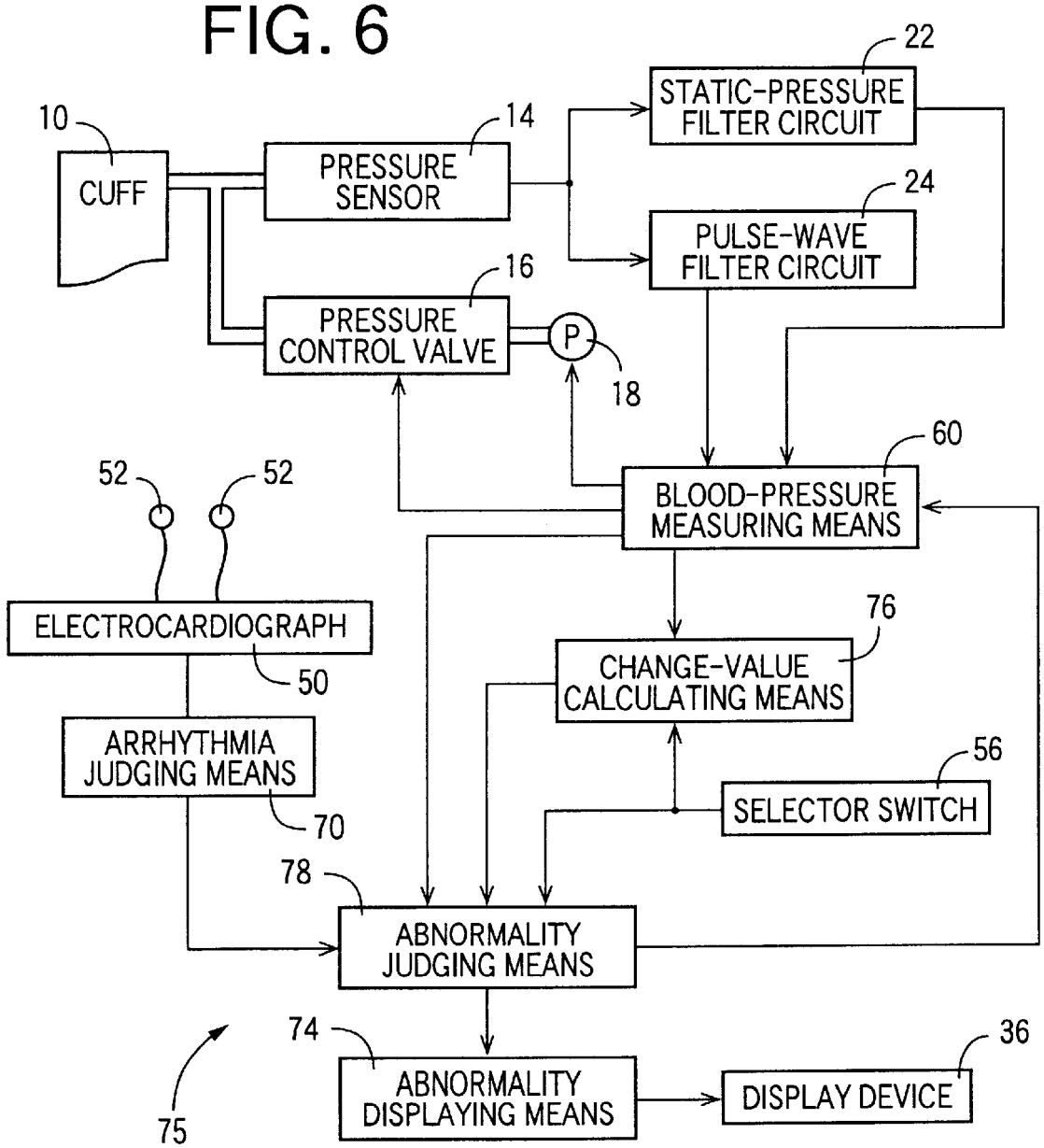
FIG. 6 is a block diagram for explaining essential functions of an electronic control device of another circulation-condition monitoring apparatus as a second embodiment of the present invention.

FIG. 6 is a block diagram for explaining important functions of the control device 28 of the circulation-condition monitoring apparatus 75 as the second embodiment of the present invention. The second apparatus 75 differs from the first apparatus 8 in that the second apparatus 75 does not employ the photoelectric-pulse-wave sensor 40 or the A/D converter 48 and in that the functions of the control device 28 of the second apparatus 75 differ from those of the control device 28 of the first apparatus 8.

In FIG. 6, a change-value calculating means 76 calculates a change value ΔBP of each of a plurality of blood pressure values BP which are periodically measured by the blood-pressure measuring means 60. Here, the change value ΔBP is defined as a change rate (%) or a change amount (mmHg) of each of the blood pressure values BP. For example, the current change amount is obtained by subtracting, from the current systolic blood pressure value $BP_{SYS}$ measured by the measuring means 60 in the current blood-pressure measuring operation, the preceding systolic blood pressure value $BP_{SYS}$ measured by the measuring means 60 in the preceding blood-pressure measuring operation; and the current change rate is obtained by dividing the current change amount by the preceding systolic blood pressure value $BP_{SYS}$.

An abnormality judging means 78 operates, when the arrhythmia judging means 70 judges that an arrhythmia has occurred to the patient, the blood-pressure measuring means 60 and the change-value calculating means 76, and judges that the condition of blood circulation of the subject is abnormal, when the change value ΔBP calculated by the change-value calculating means 76 is greater than a prescribed reference value TH(Δ). Like the abnormality judging means 72 employed in the first embodiment, the abnormality judging means 78 makes a judgment by comparing an absolute value of each change value ΔBP with the positive reference value TH(Δ) as both upper and lower limits of a prescribed reference range.

In the case where the low-blood-pressure-patient signal has been input through the selector switch 56, the abnormality judging means 78 judges that the circulation condition of the patient is abnormal, when the change value ΔBP calculated by the change-value calculating means 76 is greater than the above-indicated first reference value TH(Δ) and/or when the blood pressure value BP measured by the blood-pressure measuring means 60 is lower than a second reference value TH(BP) as a lower limit of a second reference range having no upper limit. The second reference value TH(BP) may be changed depending on which one of systolic, mean, or diastolic blood pressure $BP_{SYS}$, $BP_{MEAN}$, $BP_{DIA}$ is used by the abnormality judging means 78. For example, in the case where systolic blood pressure values $BP_{SYS}$ are used by the means 78, the second reference value TH(BP) may be from 80 to 90 mmHg.

In the second embodiment, the abnormality judging means 78 operates, when the arrhythmia judging means 70 judges that an arrhythmia has occurred to the patient, the blood-pressure measuring means 60 to measure a blood pressure value BP of the patient, and operates the change-value calculating means 76 to calculate a change value ΔBP of the measured blood pressure value BP, and judges that the condition of blood circulation of the subject is abnormal, when the calculated change value ΔBP is greater than the first reference value TH(Δ). That is, since the present apparatus 75 judges an abnormality of circulation condition of the subject based on both arrhythmia and blood-pressure change, the apparatus 75 can accurately judge the abnormality of circulation condition.

In addition, in the second embodiment, in the case where the low-blood-pressure signal is input through the selector switch 56, the abnormality judging means 78 operates, when the arrhythmia judging means 70 judges that an arrhythmia has occurred to the patient, the blood-pressure measuring means 60 and the change-value calculating means 76, and judges that the circulation condition of the patient is abnormal, when the change value ΔBP calculated by the change-value calculating means 76 is greater than the first reference value TH(Δ) and/or when the blood pressure value BP measured by the blood-pressure measuring means 60 is lower than the second reference value TH(BP). Thus, the present apparatus 75 can reliably judge the abnormality of circulation condition of the patient whose blood pressure is low.

Figure 7:
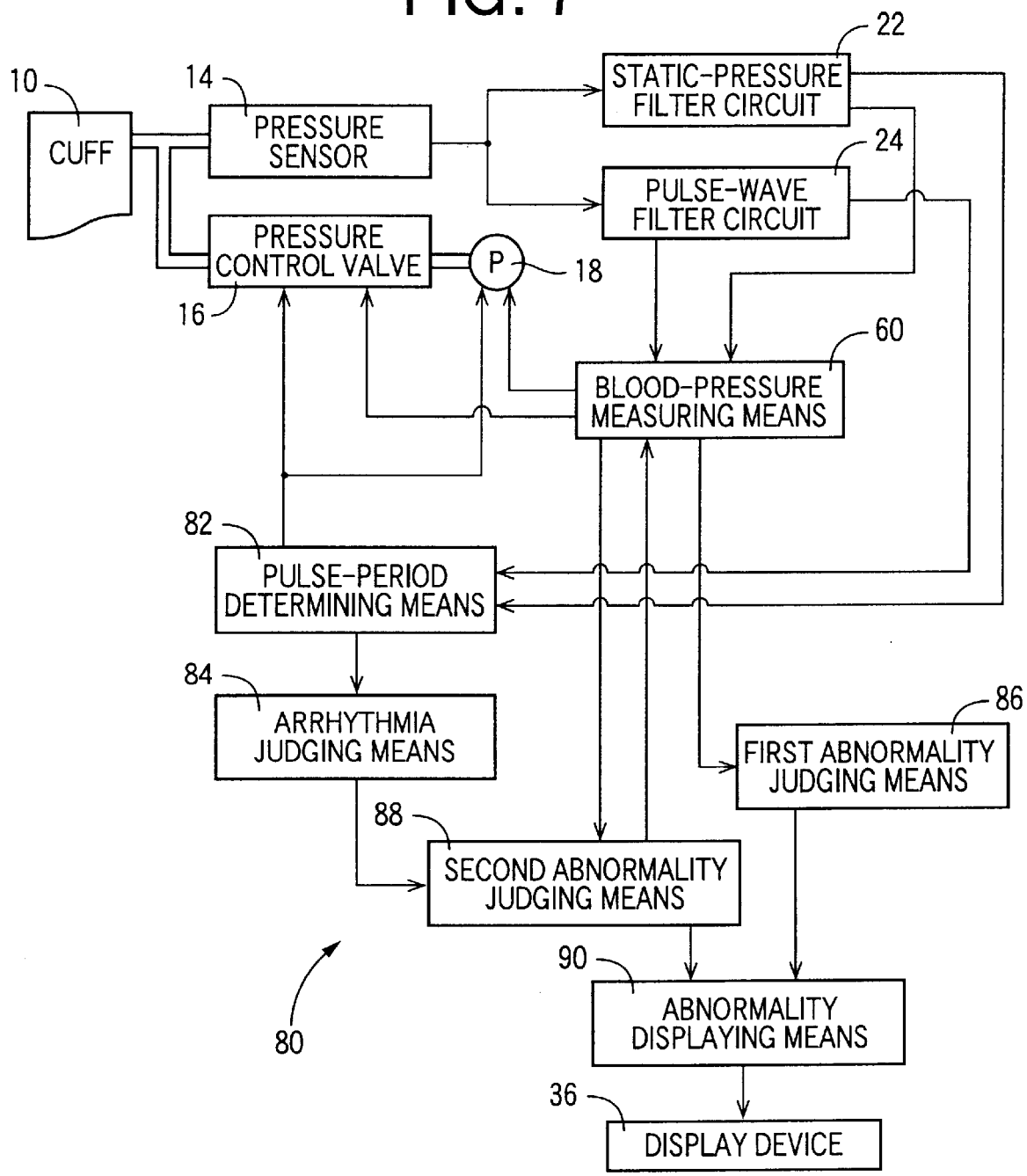
FIG. 7 is a block diagram for explaining essential functions of an electronic control device of another circulation-condition monitoring apparatus as a third embodiment of the present invention.

Next, there will be described a third embodiment of the present invention that also relates to a circulation-condition monitoring apparatus. FIG. 7 is a block diagram for explaining important functions of the control device 28 of the circulation-condition monitoring apparatus 80 as the third embodiment of the present invention. The third apparatus 80 has the same construction as that of the first apparatus 8, except that the third apparatus 80 does not employ the photoelectric-pulse-wave sensor 40, the A/D converter 48, the electrocardiograph 50, the electrodes 52, the A/D converter 54, or the selector switch 56 and in that the functions of the control device 28 of the third apparatus 80 differ from those of the control device 28 of the first apparatus 8.

In FIG. 7, a pulse-period determining means 82 operates the air pump 18 and the pressure control valve 16 so that the pressure in the cuff 10 is held at a pre-set value (e.g., from 20 to 30 mmHg) which is sufficiently lower than a diastolic blood pressure value of the patient, and detects, in this state, a brachial artery transmitted from a brachial artery of the patient, not shown, to the cuff 10, through the pressure sensor 14 and the pulse-wave filter circuit 24. The pulse-period determining means 82 iteratively determines, as a pulse period $T_P$, an interval between respective prescribed periodic points (e.g., rising points or peaks) of two successive heartbeat-synchronous pulses of the detected brachial pulse wave. Since the brachial pulse wave is a sort of heartbeat-synchronous wave, the cuff 10, the pressure sensor 14, and the pulse-wave filter circuit 24 cooperate with one another to function as a heartbeat-synchronous-wave detecting device.

An arrhythmia judging means 84 judges, based on each of the pulse period values $T_P$ determined by the pulse-period determining means 82, whether an arrhythmia has occurred to the patient. Thus, the present arrhythmia judging means 84 can identify only those sorts of arrhythmias which can be identified based on the pulse period values $T_P$; such as tachycardia, bradycardia, extrasystole, or atrial fibrillation.

A first abnormality judging means 86 judges that the condition of blood circulation of the subject is abnormal, when the blood pressure value BP measured by the blood-pressure measuring means 60 is not greater than a prescribed first reference blood pressure value $BP_1$. The first reference blood pressure value $BP_1$ may be changed depending on which one of systolic, mean, or diastolic blood pressure $BP_{SYS}$, $BP_{MEAN}$, $BP_{DIA}$ is used by the first abnormality judging means 86. For example, in the case where systolic blood pressure values $BP_{SYS}$ are used by the judging means 86, the first reference value $BP_1$ may be 70 mmHg.

A second abnormality judging means 88 operates, when the arrhythmia judging means 84 judges that an arrhythmia has occurred to the patient, the blood-pressure measuring means 60 to measure a blood pressure value of the patient, and judges that the condition of blood circulation of the subject is abnormal, when the blood pressure value BP measured by the blood-pressure measuring means 60 is not greater than a prescribed second reference blood pressure value $BP_2$ which is greater by from 5 to 30 mmHg than the first reference blood pressure value $BP_1$. Like the first reference blood pressure value $BP_1$, the second reference blood pressure value $BP_2$ may be changed depending on which one of systolic, mean, or diastolic blood pressure $BP_{SYS}$, $BP_{MEAN}$, $BP_{DIA}$ is used by the second abnormality judging means 88.

An abnormality displaying means 90 operates, when the first or second abnormality judging means 86, 88 judges that the condition of blood circulation of the subject is abnormal, the display device 36 to display an indication that the condition of blood circulation of the subject is abnormal.

Figure 8:
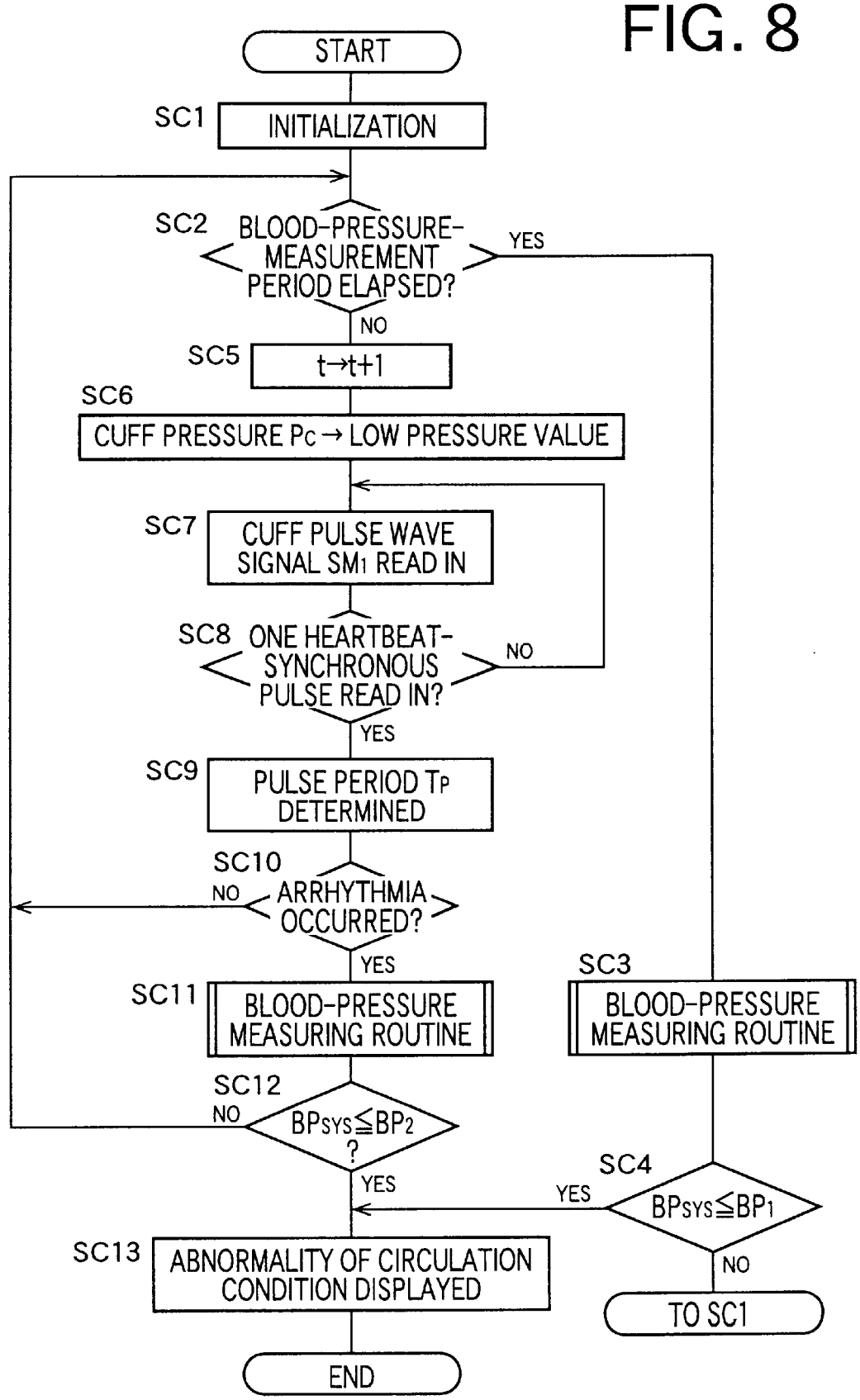
FIG. 8 is a flow chart representing a controlling operation of the control device of the circulation-condition monitoring apparatus of FIG. 7.

FIG. 8 shows a flow chart representing a control program according to which the control device 28 controls the circulation-condition monitoring apparatus 80. First, at Step SC1, the control device 28 initializes the apparatus 80, more specifically, resets a timer, t, and various registers.

Subsequently, at Step SC2, the control device 28 judges, based on a time measured by the timer t, whether a time which has elapsed after the last blood pressure measuring operation using the cuff 10 has reached or exceeded a prescribed blood-pressure-measurement starting period of from 15 to 20 minutes. If a positive judgment is made at Step SC2, the control of the control device 28 goes to Step SC3 corresponding to the blood-pressure measuring means 60, where the control device 28 carries out a blood pressure measuring routine in which blood pressure values BP (e.g., systolic blood pressure value $BP_{SYS}$) of the patient are measured using the cuff 10. This blood pressure measuring routine is the same as that carried out at Steps SA2 and SA4 to SA8 of FIG. 4.

Step SC3 is followed by Step SC4 corresponding to the first abnormality judging means 86, where the control device 28 judges whether the systolic blood pressure value $BP_{SYS}$ measured at Step SC3 is not greater than 70 mmHg as the first reference blood pressure value $BP_1$. If a negative judgment is made at Step SC4, Step SC1 and the following steps are repeated. On the other hand, if a positive judgment is made at Step SC4, the control goes to Step SC13, described later.

If a negative judgment is made at Step SC2, that is, if the blood-pressure-measurement starting period has not elapsed, the control goes to Step SC5 to add one to the content counted by the timer t. Subsequently, the control of the control device 28 goes to Steps SC6 to SC9 corresponding to the pulse-period determining means 82.

First, at Step SC6, the control device 28 operates the air pump 18 and the pressure control valve 16 so that the pressure in the cuff 10 is changed to, and kept at, a low pre-set pressure value of from 20 to 30 mmHg. Step SC6 is followed by Step SC7 to start reading in the brachial pulse wave represented by the cuff pulse wave signal $SM_1$ which is detected by the pressure sensor 14 and extracted by the pulse-wave filter circuit 24 in the state established at Step SC6.

Subsequently, at Step SC8, the control device 28 judges whether it has read in one heartbeat-synchronous pulse of the cuff pulse wave signal $SM_1$ at Step SC7. Steps SC7 and SC8 are repeated to continue reading in the signal $SM_1$ until a positive judgment is made at Step SC8. When a positive judgment is made, the control of the control device 28 goes to Step SC9 corresponding to the pulse-period determining means 82, where the control device 28 determines a prescribed periodic point (e.g., peak) on the one heartbeat-synchronous pulse of the brachial pulse wave of the cuff pulse wave signal $SM_1$ read in at Steps SC7 and SC8, and determines, as a pulse period $T_P$, a time interval between the time of occurrence of the prescribed periodic point of the preceding one heartbeat-synchronous pulse and the time of occurrence of the prescribed periodic point of the current one heartbeat-synchronous pulse.

Step SC9 is followed by Step SC10 corresponding to the arrhythmia judging means 84, where the control device 28 judges, based on a change of the current pulse period $T_P$ determined at Step SC9, from the preceding pulse period $T_P$, whether an arrhythmia has occurred to the patient. If a negative judgment is made at Step SC10, Steps SC2 and the following steps are repeated. On the other hand, if a positive judgment is made at Step SC10, the control goes to Step SC11 corresponding to the blood pressure measuring means 60, where the control device 28 carries out the same blood pressure measuring routine as that carried out at Step SC3.

Step SC11 is followed by Step SC12 corresponding to the second abnormality judging means 88, where the control device 28 judges whether the systolic blood pressure value $BP_{SYS}$ measured at Step SC11 is not greater than 80 mmHg as the prescribed second reference blood pressure value $BP_2$. If a negative judgment is made at Step SC12, Step SC2 and the following steps are repeated.

On the other hand, if a positive judgment is made at Step SC12, or if a positive judgment is made at Step SC4, the control goes to Step SC13 corresponding to the abnormality displaying means 90, where the control device 28 operates the display device 36 to display the message that the circulation condition of the patient is abnormal. Thus, the current control cycle according to the routine of FIG. 8 is ended.

In the third embodiment, the first abnormality judging means 86 (Step SC4) judges that the circulation condition of the subject is abnormal, when the systolic blood pressure value $BP_{SYS}$ measured by the blood-pressure measuring means 60 (Step SC3) is not greater than the prescribed first reference blood-pressure value $BP_1$. In addition, even if the first abnormality judging means 86 (Step SC4) does not judge that the circulation condition of the subject is abnormal, the second abnormality judging means 88 (Step SC12) operates, when the arrhythmia judging means 84 (Step SC10) judges that an arrhythmia has occurred to the subject, the blood-pressure measuring means 60 (Step SC11) to measure a systolic blood pressure value $BP_{SYS}$ of the subject, and judges that the circulation condition of the subject is abnormal, when the thus measured systolic blood pressure value $BP_{SYS}$ is not greater than the prescribed second reference blood pressure value $BP_2$ greater than the first reference blood pressure value $BP_1$. Thus, the present apparatus 80 can accurately judge the abnormality of circulation condition.

In addition, in the third embodiment, the cuff 10 as part of the blood-pressure measuring means 60 is used to detect the brachial pulse wave (i.e., heartbeat-synchronous wave). Therefore, the circulation-condition monitoring apparatus 80 can enjoy a simple construction and can be produced at reduced cost.

Figure 9:
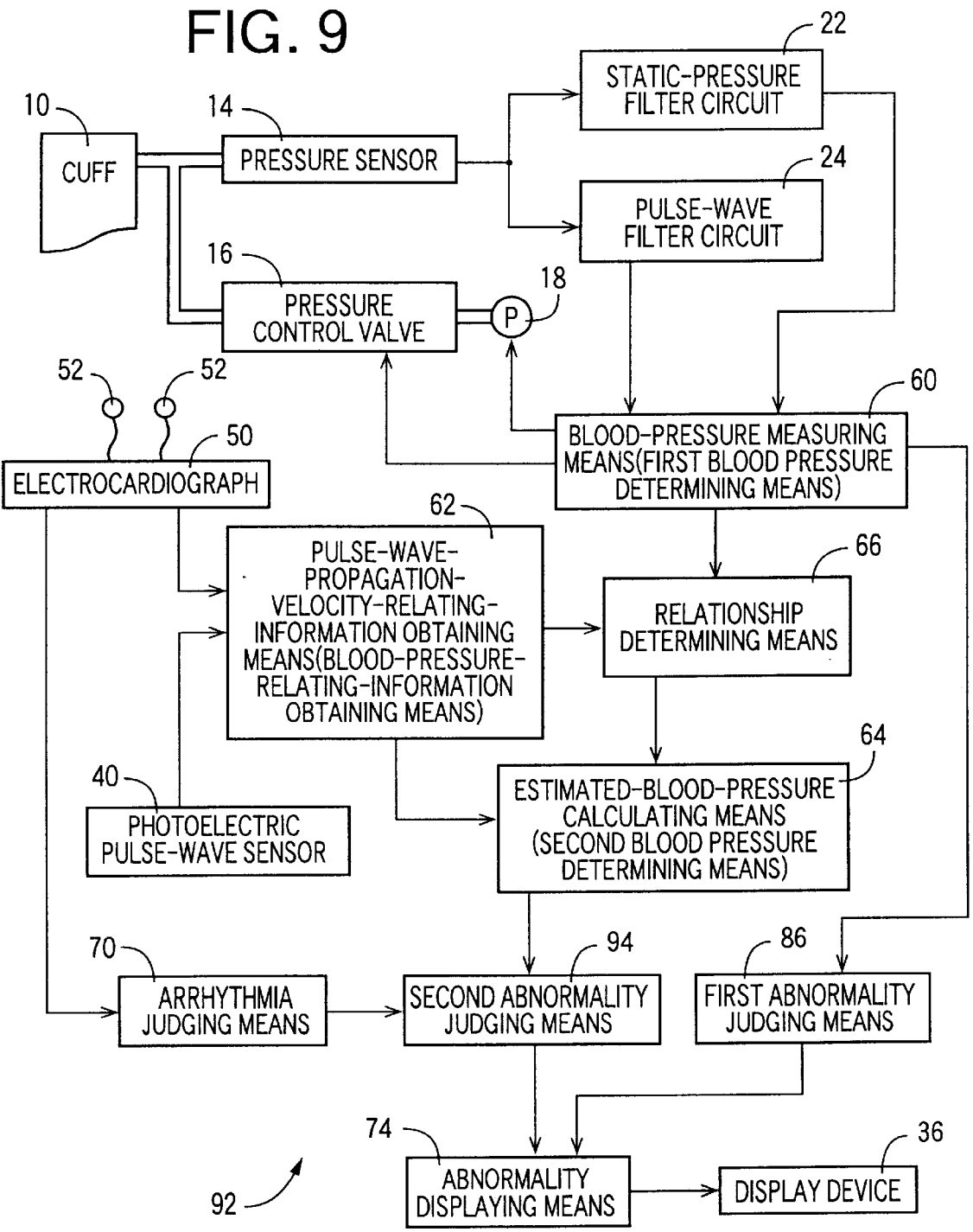
FIG. 9 is a block diagram for explaining essential functions of an electronic control device of another circulation-condition monitoring apparatus as a fourth embodiment of the present invention.

Next, there will be described a fourth embodiment of the present invention that also relates to a circulation-condition monitoring apparatus. FIG. 9 is a block diagram for explaining important functions of the control device 28 of the circulation-condition monitoring apparatus 92 as the fourth embodiment of the present invention. The fourth apparatus 92 differs from the first apparatus 8 in that the fourth apparatus 92 does not employ the selector switch 56 and in that the functions of the control device 28 of the fourth apparatus 92 differ from those of the control device 28 of the first apparatus 8.

In FIG. 9, a second abnormality judging means 94 judges that the circulation condition of the patient is abnormal, when the arrhythmia judging means 70 judges that an arrhythmia has occurred to the patient and simultaneously when the estimated blood pressure value EBP calculated by the estimated-blood-pressure calculating means 64 based on the piece of blood-pressure-relating information obtained at the time of detection of the arrhythmia is not greater than a prescribed second reference value $BP_2$. The second reference value $BP_2$ is the same as that employed in the third embodiment. That is, the second reference value $BP_2$ is greater by from 5 to 30 mmHg than the first reference value $BP_1$ and, like the first reference value $BP_1$, may be changed depending upon which one of systolic, mean, and diastolic blood pressure $BP_{SYS}$, $BP_{MEAN}$, $BP_{DIA}$ is utilized by the second abnormality judging means 94.

In the fourth embodiment, the first abnormality judging means 86 judges that the circulation condition of the subject is abnormal, when the blood pressure value BP measured by the blood-pressure measuring means 60 is not greater than the first reference blood-pressure value $BP_1$. In addition, even if the first abnormality judging means 86 does not judge that the circulation condition of the subject is abnormal, the second abnormality judging means 94 judges that the circulation condition of the subject is abnormal, when the arrhythmia judging means 70 judges that an arrhythmia has occurred to the subject and simultaneously when the estimated blood pressure value EBP calculated by the estimated-blood-pressure calculating means 64 is not greater than the prescribed second reference blood pressure value $BP_2$ greater than the first reference blood pressure value $BP_1$. Thus, the present apparatus 92 can accurately monitor the circulation condition of the subject. In addition, each piece of pulse-wave-propagation-velocity-relating information is obtained based on the photoelectric pulse wave and electrocardiogram which are detected by the photoelectric pulse-wave sensor 40 and the electrocardiograph 50 without occluding the arteries of the subject, each estimated blood pressure value EBP is calculated based on the thus obtained piece of pulse-wave-propagation-velocity-relating information. Thus, the present apparatus 92 does not always occlude the arteries of the patient when the arrhythmia judging means 70 judges that arrhythmia has occurred. Accordingly, the discomfort the subject feels is reduced as such.

While the present invention has been described in detail in its preferred embodiments, by reference to the drawings, it is to be understood that the present invention may otherwise be embodied.

For example, in each of the first, second, and fourth embodiments, the electrocardiograph 50 is utilized as the heartbeat-synchronous-wave detecting device; and in the third embodiment, the cuff 10, the pressure sensor 14, and the pulse-wave filter circuit 24 are utilized as the heartbeat-synchronous-wave detecting device. However, in each of the first, second, and fourth embodiments, the pressure sensor 14, and the pulse-wave filter circuit 24 may be utilized as the heartbeat-synchronous-wave detecting device; and in the third embodiment, the electrocardiograph 50 is employed as the heartbeat-synchronous-wave detecting device.

In each of the first to fourth embodiments, the electrocardiograph 50, or the cuff 10, the pressure sensor 14 and the pulse-wave filter circuit 24 is or are utilized as the heartbeat-synchronous-wave detecting device. However, since a pulse wave which propagates in a living subject is a heartbeat-synchronous wave, a pulse-wave detecting device which detects the pulse wave may be employed as the heartbeat-synchronous-wave detecting device. For example, the photoelectric pulse-wave sensor 40 may be utilized as the heartbeat-synchronous-wave detecting device. Otherwise, a photoelectric-pulse-wave detecting probe for use with an oximeter, an impedance-pulse-wave detecting device which detects an impedance change through electrodes worn on a living subject, or a pressure-pulse-wave detecting device which is pressed against a carotid or radial artery of a living subject and detects a pressure in the artery may be employed as the heartbeat-synchronous-wave detecting device.

In each of the first and fourth embodiments, the pulse-wave-propagation-velocity-relating information is obtained as the blood-pressure-relating information. However, since an area, S, defined by each heartbeat-synchronous pulse of the pulse wave detected by the photoelectric-pulse-wave sensor 40 or the like changes in relation with the blood pressure of a living subject, the area S may be obtained as the blood-pressure-relating information. Otherwise, a normalized pulse-wave area VR which is obtained by normalizing the area S based on a period, W, and an amplitude, L, of the each heartbeat-synchronous pulse may be obtained as the blood-pressure-relating information. In addition, since pulse period $T_P$ or heart rate HR changes in relation with blood pressure of a living subject, the pulse period $T_P$ or the heart rate HR may be used as the blood-pressure-relating information.

In each of the first to fourth embodiments, the abnormality displaying means 74, 90 operates, when it is judged that the circulation condition of the patient is abnormal, the display device 36 to display the indication that the circulation condition of the patient is abnormal. However, in place of, or in addition to, the displaying of the indication, it is possible to produce an alarming sound.

In the first embodiment, the abnormality judging means 72 operates, when it judges that the circulation condition of the patient is abnormal, the blood-pressure measuring means 60 to measure a blood pressure of the patient. However, the abnormality judging means 72 may be so modified as not to operate it at that time.

It is to be understood that the present invention may be embodied with other changes, improvements and modifications that may occur to one skilled in the art without departing from the spirit and scope of the invention defined in the appended claims.

What is claimed is:

1. An apparatus for monitoring a condition of blood circulation of a living subject, comprising:
   a heartbeat-synchronous-wave detecting device which detects a heartbeat-synchronous wave from the subject;
   an arrhythmia judging means for judging whether an arrhythmia has occurred to the subject, based on the heartbeat-synchronous wave detected by the heartbeat-synchronous-wave detecting device;
   a first blood-pressure determining means including an inflatable cuff which is adapted to be wound around a first body portion of the subject to occlude an artery of the first body portion, the first blood-pressure determining means determining at least one first blood pressure of the subject based on a first pulse wave which is produced in the cuff when a pressure in the cuff is decreased;
   a blood-pressure-relating-information obtaining means including at least one pulse-wave detecting device which is adapted to be worn on at least one second body portion of the subject to detect at least one second pulse wave from the at least one second body portion without occluding at least one artery of the at least one second body portion, the blood-pressure-relating-information obtaining means iteratively obtaining, based on the at least one second pulse wave detected by the at least one pulse-wave detecting device, a piece of blood-pressure-relating information which changes in relation with blood pressure of the subject;
   a relationship determining means for determining a relationship between blood pressure and blood-pressure-relating information, based on at least one first blood pressure value determined by the first blood-pressure determining means and at least one piece of blood-pressure-relating information obtained by the blood-pressure-relating-information obtaining means;
   a second blood-pressure determining means for iteratively determining, according to the relationship determined by the relationship determining means, a second blood pressure of the subject based on each of the pieces of blood-pressure-relating information iteratively obtained by the blood-pressure-relating-information obtaining means;
   a change-value calculating means for calculating a change value of each of the second blood pressure values iteratively determined by the second blood-pressure determining means; and
   an abnormality judging means for judging that the condition of blood circulation of the subject is abnormal, when the arrhythmia judging means judges that the arrhythmia has occurred to the subject and when the change value calculated by the change-value calculating means does not fall within a first reference range.

2. An apparatus according to claim 1, further comprising an input device which is operable for inputting a low-blood-pressure-subject signal indicating that the blood pressure of the living subject is low, wherein the abnormality judging means judges, when the low-blood-pressure-subject signal is input through the input device, that the condition of blood circulation of the subject is abnormal, when the arrhythmia judging means judges that the arrhythmia has occurred to the subject and when at least one of the change value calculated by the change-value calculating means and said each second blood pressure value determined by the second blood-pressure determining means does not fall within a corresponding one of the first reference range and a second reference range.

3. An apparatus according to claim 1, wherein the heartbeat-synchronous-wave detecting device comprises an electrocardiograph which includes a plurality of electrodes that are adapted to be worn at a plurality of prescribed locations on the living subject and which detects, as the heartbeat-synchronous wave, an electrocardiogram through the electrodes.

4. An apparatus according to claim 1, wherein the heartbeat-synchronous-wave detecting device comprises the inflatable cuff and detects, as the heartbeat-synchronous wave, the first pulse wave which is produced in the cuff in a state in which the pressure in the cuff is equal to a pre-set value lower than a diastolic blood pressure value of the living subject.

5. An apparatus for monitoring a condition of blood circulation of a living subject, comprising:
- a heartbeat-synchronous-wave detecting device which detects a heartbeat-synchronous wave from the subject;
- an arrhythmia judging means for judging whether an arrhythmia has occurred to the subject, based on the heartbeat-synchronous wave detected by the heartbeat-synchronous-wave detecting device;
- a blood-pressure measuring means including an inflatable cuff which is adapted to be wound around a body portion of the subject, and iteratively measuring a blood pressure of the subject based on a pulse wave which is produced in the cuff when a pressure in the cuff is changed;
- a change-value calculating means for iteratively calculating a change value of each of the blood pressure values iteratively measured by the blood-pressure measuring means; and
- an abnormality judging means for operating, when the arrhythmia judging means judges that the arrhythmia has occurred to the subject, the blood-pressure measuring means to measure a blood pressure of the subject, and the change-value calculating means to calculate a change value of the measured blood pressure value, and judging that the condition of blood circulation of the subject is abnormal, when the change value calculated by the change-value calculating means does not fall within a first reference range.

6. An apparatus according to claim 5, further comprising an input device which is operable for inputting a low-blood-pressure-subject signal indicating that the blood pressure of the living subject is low, wherein the abnormality judging means operates, when the arrhythmia judging means judges that the arrhythmia has occurred to the subject, the blood-pressure measuring means and the change-value calculating means, and judges that the condition of blood circulation of the subject is abnormal, when at least one of the change value calculated by the change-value calculating means and the blood pressure value measured by the blood-pressure measuring means does not fall within a corresponding one of the first reference range and a second reference range.

7. An apparatus according to claim 5, wherein the heartbeat-synchronous-wave detecting device comprises an electrocardiograph which includes a plurality of electrodes that are adapted to be worn at a plurality of prescribed locations on the living subject and which detects, as the heartbeat-synchronous wave, an electrocardiogram through the electrodes.

8. An apparatus according to claim 5, wherein the heartbeat-synchronous-wave detecting device comprises the inflatable cuff and detects, as the heartbeat-synchronous wave, the pulse wave which is produced in the cuff in a state in which the pressure in the cuff is equal to a pre-set value lower than a diastolic blood pressure value of the living subject.

9. An apparatus for monitoring a condition of blood circulation of a living subject, comprising:
- a heartbeat-synchronous-wave detecting device which detects a heartbeat-synchronous wave from the subject;
- an arrhythmia judging means for judging whether an arrhythmia has occurred to the subject based on the heartbeat-synchronous wave detected by the heartbeat-synchronous-wave detecting device;
- a blood-pressure measuring means including an inflatable cuff which is adapted to be wound around a body portion of the subject, and measuring a first blood pressure of the subject based on a pulse wave which is produced in the cuff when a pressure in the cuff is changed;
- a first abnormality judging means for judging that the condition of blood circulation of the subject is abnormal, when the first blood pressure value measured by the blood-pressure measuring means is not greater than a first reference value; and
- a second abnormality judging means for operating, when the arrhythmia judging means judges that the arrhythmia has occurred to the subject, the blood-pressure measuring means to measure a second blood pressure of the subject, and judging that the condition of blood circulation of the subject is abnormal, when the second blood pressure value measured by the blood-pressure measuring means is not greater than a second reference value greater than the first reference value.

10. An apparatus according to claim 9, wherein the heartbeat-synchronous-wave detecting device comprises an electrocardiograph which includes a plurality of electrodes that are adapted to be worn at a plurality of prescribed locations on the living subject and which detects, as the heartbeat-synchronous wave, an electrocardiogram through the electrodes.

11. An apparatus according to claim 9, wherein the heartbeat-synchronous-wave detecting device comprises the inflatable cuff and detects, as the heartbeat-synchronous wave, the pulse wave which is produced in the cuff in a state in which the pressure in the cuff is equal to a pre-set value lower than a diastolic blood pressure value of the living subject.

12. An apparatus for monitoring a condition of blood circulation of a living subject, comprising:
- a heartbeat-synchronous-wave detecting device which detects a heartbeat-synchronous wave from the subject;
- an arrhythmia judging means for judging whether an arrhythmia has occurred to the subject based on the heartbeat-synchronous wave detected by the heartbeat-synchronous-wave detecting device;
- a first blood-pressure determining means including an inflatable cuff which is adapted to be wound around a first body portion of the subject to occlude an artery of the first body portion, the first blood-pressure determining means determining at least one first blood pressure of the subject based on a first pulse wave which is produced in the cuff when a pressure in the cuff is decreased;
- a blood-pressure-relating-information obtaining means including at least one pulse-wave detecting device which is adapted to be worn on at least one second body portion of the subject to detect at least one second pulse wave from the at least one second body portion without occluding at least one artery of the at least one second body portion, the blood-pressure-relating-information obtaining means iteratively obtaining, based on the at least one second pulse wave detected by the at least one pulse-wave detecting device, a piece of blood-pressure-relating information which changes in relation with blood pressure of the subject;
- a relationship determining means for determining a relationship between blood pressure and blood-pressure-relating information, based on at least one first blood pressure value determined by the first blood-pressure determining means and at least one piece of blood-pressure-relating information obtained by the blood-pressure-relating-information obtaining means;

a second blood-pressure determining means for iteratively determining, according to the relationship determined by the relationship determining means, a second blood pressure of the subject based on each of a plurality of pieces of blood-pressure-relating information iteratively obtained by the blood-pressure-relating-information obtaining means;

a first abnormality judging means for judging that the condition of blood circulation of the subject is abnormal, when a first blood pressure value determined by the first blood-pressure determining means is not greater than a first reference value; and a second abnormality judging means for judging that the condition of blood circulation of the subject is abnormal, when the arrhythmia judging means judges that the arrhythmia has occurred to the subject and when a second blood pressure value determined by the second blood-pressure determining means is not greater than a second reference value greater than the first reference value.

13. An apparatus according to claim 12, wherein the heartbeat-synchronous-wave detecting device comprises an electrocardiograph which includes a plurality of electrodes that are adapted to be worn at a plurality of prescribed locations on the living subject and which detects, as the heartbeat-synchronous wave, an electrocardiogram through the electrodes.

14. An apparatus according to claim 12, wherein the heartbeat-synchronous-wave detecting device comprises the inflatable cuff and detects, as the heartbeat-synchronous wave, the first pulse wave which is produced in the cuff in a state in which the pressure in the cuff is equal to a pre-set value lower than a diastolic blood pressure value of the living subject.

* * * * *